(12) United States Patent
Crowder et al.

(10) Patent No.: US 8,210,172 B2
(45) Date of Patent: *Jul. 3, 2012

(54) DRY POWDER INHALERS

(75) Inventors: Timothy M. Crowder, Durham, NC (US); Anthony J. Hickey, Chapel Hill, NC (US); Jeffrey A. Warden, Chapel Hill, NC (US)

(73) Assignee: Oriel Therapeutics, Inc., Durham, NC (US)

( * ) Notice: Subject to any disclaimer, the term of this patent is extended or adjusted under 35 U.S.C. 154(b) by 329 days.

This patent is subject to a terminal disclaimer.

(21) Appl. No.: 12/401,138

(22) Filed: Mar. 10, 2009

(65) Prior Publication Data

US 2009/0165790 A1    Jul. 2, 2009

Related U.S. Application Data

(60) Continuation of application No. 11/043,363, filed on Jan. 26, 2005, now Pat. No. 7,520,278, which is a division of application No. 10/434,009, filed on May 8, 2003, now Pat. No. 6,889,690.

(60) Provisional application No. 60/379,521, filed on May 10, 2002, provisional application No. 60/392,671, filed on Jun. 27, 2002, provisional application No. 60/440,513, filed on Jan. 16, 2003.

(51) Int. Cl.
*A61M 16/00* (2006.01)
*A61M 15/00* (2006.01)

(52) U.S. Cl. .......... 128/203.15; 128/203.12; 128/200.24

(58) Field of Classification Search ............. 128/200.24, 128/203.12, 203.15, 203.19, 203.21, 203.23, 128/200.11, 200.14, 200.19, 200.23, 202.22, 128/205.23; 604/58; 206/581, 461

See application file for complete search history.

(56) References Cited

U.S. PATENT DOCUMENTS

| 3,948,264 A | 4/1976 | Wilke et al. |
| 4,009,280 A * | 2/1977 | Macarthur et al. ............ 514/456 |
| 4,778,054 A | 10/1988 | Newell et al. |
| 4,836,417 A | 6/1989 | Uchiyama et al. |
| 5,033,463 A | 7/1991 | Cocozza |

(Continued)

FOREIGN PATENT DOCUMENTS

EP    0129985    1/1985

(Continued)

OTHER PUBLICATIONS

Crowder, et al., *2001: an Odyssey in Inhaler Formulation and Design*, Pharmaceutical Technology, pp. 99-113, Jul. 2001.

(Continued)

*Primary Examiner* — Annette Dixon
(74) *Attorney, Agent, or Firm* — Myers Bigel Sibley & Sajovec, P.A.

(57) ABSTRACT

Dry powder inhalers include an elongate body and a disk holding a plurality of doses of a dry powder inhalable product. The inhaler also includes a cover member that is pivotably attached to the elongate body so that it remains attached to the body during normal operational periods of use and moves to a first closed position to overlie the inhalation port at the bottom end portion of the body during periods of non-use and moves to a second open position away from the inhalation port during periods of use to allow a user to access the inhalation port.

19 Claims, 14 Drawing Sheets

U.S. PATENT DOCUMENTS

| | | |
|---|---|---|
| 5,201,322 A | 4/1993 | Henry et al. |
| D342,994 S | 1/1994 | Rand et al. |
| 5,388,572 A | 2/1995 | Mulhauser et al. |
| 5,408,994 A | 4/1995 | Wass et al. |
| 5,469,843 A | 11/1995 | Hodson |
| 5,482,032 A | 1/1996 | Smith et al. |
| 5,533,502 A | 7/1996 | Piper |
| D377,215 S | 1/1997 | Rand |
| 5,622,166 A | 4/1997 | Eisele et al. |
| D379,506 S | 5/1997 | Maher |
| 5,655,523 A | 8/1997 | Hodson et al. |
| D391,369 S | 2/1998 | Anderson |
| 5,743,250 A | 4/1998 | Gonda et al. |
| 5,752,505 A * | 5/1998 | Ohki et al. ............... 128/203.15 |
| 5,797,391 A * | 8/1998 | Cook et al. ............... 128/203.15 |
| 5,896,855 A | 4/1999 | Hobbs et al. |
| 5,921,237 A * | 7/1999 | Eisele et al. ............. 128/203.21 |
| 6,026,809 A | 2/2000 | Abrams et al. |
| 6,029,663 A | 2/2000 | Eisele et al. |
| 6,092,522 A * | 7/2000 | Calvert et al. ............ 128/203.21 |
| D433,126 S | 10/2000 | McCurry |
| 6,142,146 A | 11/2000 | Abrams et al. |
| 6,158,293 A | 12/2000 | Poole |
| D437,931 S | 2/2001 | Anderson |
| 6,182,655 B1 * | 2/2001 | Keller et al. ............. 128/203.15 |
| D445,496 S | 7/2001 | Anderson |
| 6,261,274 B1 | 7/2001 | Arghyris et al. |
| 6,296,152 B1 | 10/2001 | Semenenko |
| 6,328,033 B1 | 12/2001 | Avrahami |
| 6,328,034 B1 * | 12/2001 | Eisele et al. ............. 128/203.15 |
| 6,488,181 B1 | 12/2002 | Schuller et al. |
| 6,561,186 B2 | 5/2003 | Casper et al. |
| 6,626,173 B2 | 9/2003 | Genova et al. |
| D494,674 S | 8/2004 | King et al. |
| 6,805,175 B1 | 10/2004 | Pinkas et al. |
| D497,988 S | 11/2004 | King et al. |
| 6,880,555 B1 * | 4/2005 | Brunnberg et al. ...... 128/203.12 |
| 6,880,722 B2 * | 4/2005 | Anderson et al. ................ 221/71 |
| 6,889,690 B2 | 5/2005 | Crowder et al. |
| 6,964,550 B2 | 11/2005 | Hafner |
| 6,985,798 B2 | 1/2006 | Crowder et al. |
| 7,069,929 B2 * | 7/2006 | Young et al. ............. 128/203.15 |
| D560,793 S | 1/2008 | Pearl et al. |
| D569,967 S | 5/2008 | Pearl et al. |
| 7,520,278 B2 * | 4/2009 | Crowder et al. ......... 128/203.15 |
| 2004/0055598 A1 | 3/2004 | Crowder et al. |
| 2005/0267628 A1 | 12/2005 | Crowder et al. |
| 2007/0221218 A1 * | 9/2007 | Warden et al. ........... 128/203.15 |

FOREIGN PATENT DOCUMENTS

| | | |
|---|---|---|
| EP | 1106196 | 9/2001 |
| EP | 1166812 | 1/2002 |
| EP | 1172122 | 1/2002 |
| WO | WO 01/68169 | 9/2001 |

OTHER PUBLICATIONS

Peart et al., *New Developments in Dry Powder Inhaler Technology*, American Pharmaceutical Review, vol. 4, No. 3, pp. 37-45 (2001).
Prime et al.,*Review of Dry Powder Inhalers*, 26 Adv. Drug Delivery Rev., pp. 51-58 (1997).
Hickey et al., *A new millennium for inhaler technology*, 21 Pharm. Tech., n. 6, pp. 116-125 (1997).
International Search Report for related PCT application No. PCT/2003/014619, mail date Dec. 12, 2003.
International Preliminary Examination Report for related PCT application No. PCT/2003/014619, mail date Sep. 22, 2004.
http://advair.ibreathe.com/consumer/2_2_2_taking_advair_animation.htm, ADVAIR DISKUS 100/50, 3 sheets, 1997.

* cited by examiner

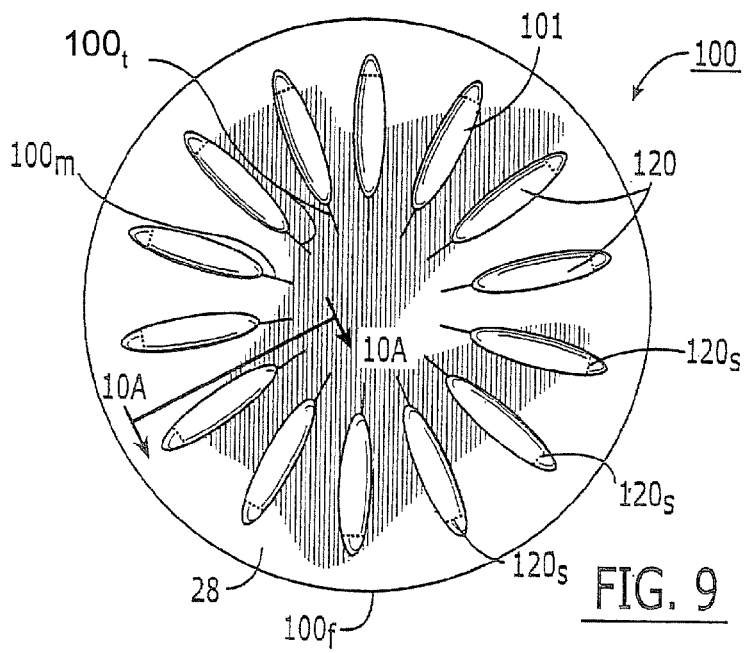
FIG. 9
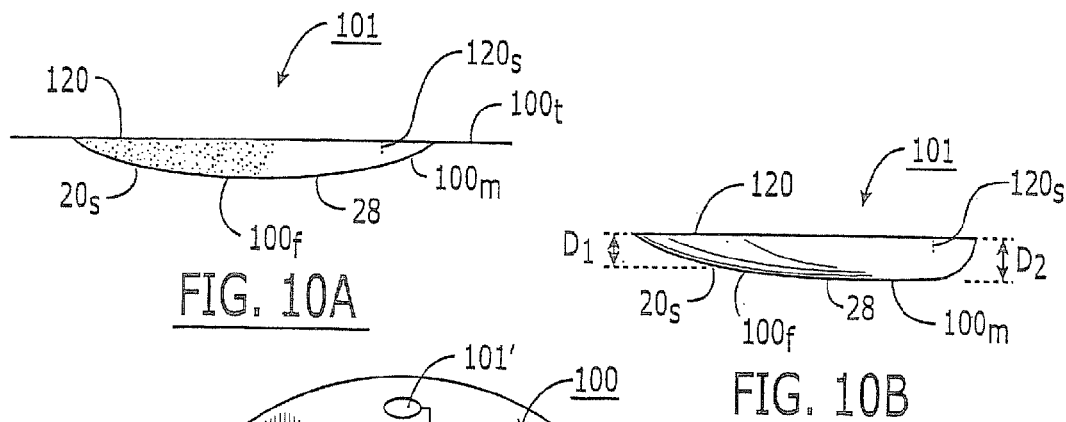
FIG. 10A
FIG. 10B
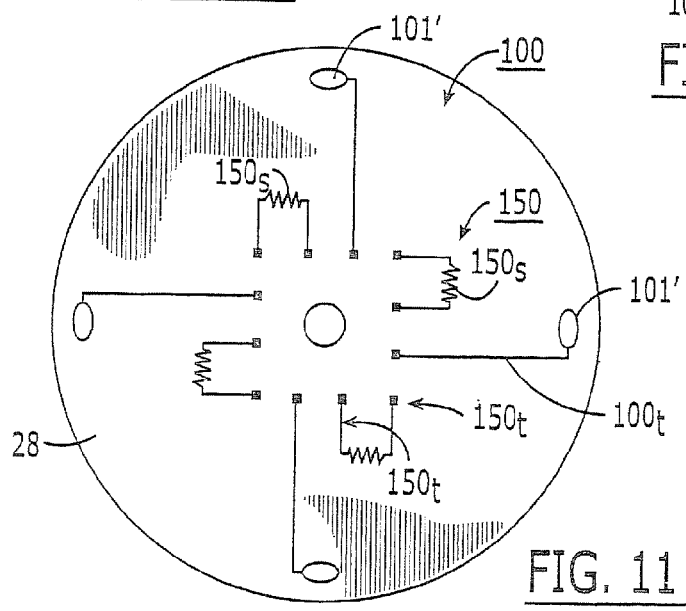
FIG. 11

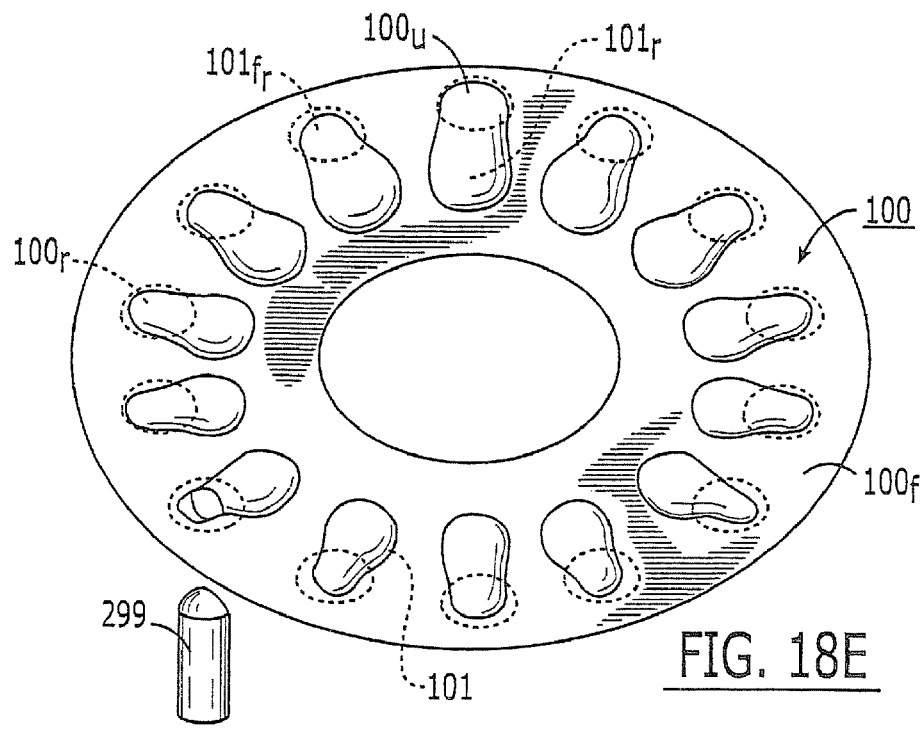
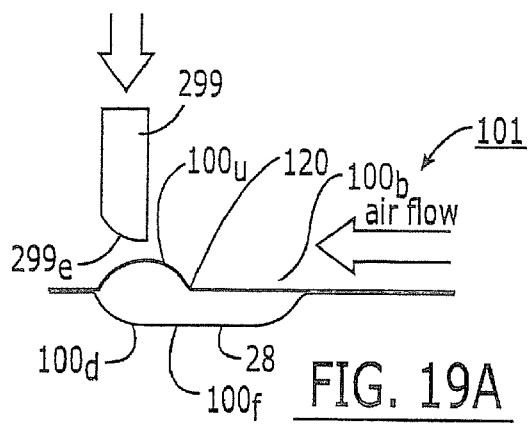
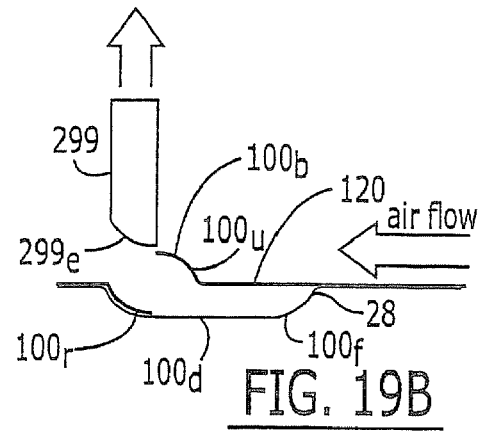
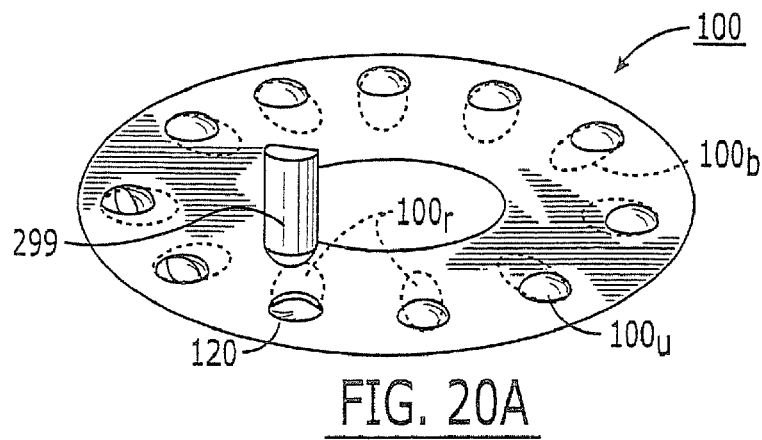

SIGNAL GENERATION

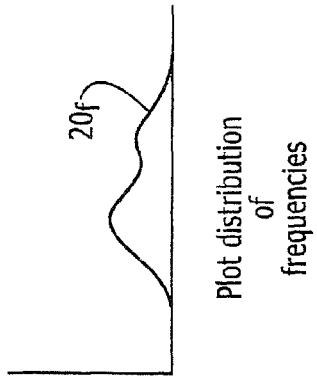

FIG. 21A

Measure time between avalanches for powders in rotating drum

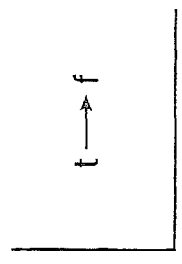

FIG. 21B $t \longrightarrow f$

Convert time to frequency space

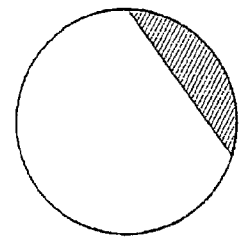

FIG. 21C

Plot distribution of frequencies

FIG. 21D

Record top six most observed frequencies, typically representing 75% of distribution

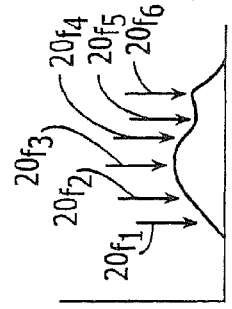

FIG. 21E

Superimpose these six frequencies to construct a single superposition signal (can include step of adjusting relative amplitudes)

DRY POWDER INHALERS

RELATED APPLICATIONS

This application is a continuation of U.S. patent application Ser. No. 11/043,363, filed Jan. 26, 2005, which issued as U.S. Pat. No. 7,520,278 on Apr. 21, 2009, which is a divisional of U.S. patent application Ser. No. 10/434,009, filed May 8, 2003, which issued as U.S. Pat. No. 6,889,690, on May 10, 2005, which claims the benefit of priority to U.S. Provisional Application Ser. No. 60/379,521, filed May 10, 2002, U.S. Provisional Application Ser. No. 60/392,671, filed Jun. 27, 2002, and U.S. Provisional Application Ser. No. 60/440,513, filed Jan. 16, 2003, the contents of which are hereby incorporated by reference as if recited in full herein.

FIELD OF THE INVENTION

The present invention relates to the delivery of dry powder substances, such as dose-regulated pharmaceutical products, as inhalant aerosols.

BACKGROUND OF THE INVENTION

Dry powder inhalers (DPI's) represent a promising alternative to pressurized pMDI (pressurized meted dose inhaler) devices for delivering drug aerosols without using CFC propellants. See generally, Crowder et al., 2001: *an Odyssey in Inhaler Formulation and Design*, Pharmaceutical Technology, pp. 99-113, July 2001;and Peart et al., *New Developments in Dry Powder Inhaler Technology*, American Pharmaceutical Review, Vol. 4, n. 3, pp. 37-45 (2001). Typically, the DPIs are configured to deliver a powdered drug or drug mixture that includes an excipient and/or other ingredients. Conventionally, many DPIs have operated passively, relying on the inspiratory effort of the patient to dispense the drug provided by the powder. Unfortunately, this passive operation can lead to poor dosing uniformity since inspiratory capabilities can vary from patient to patient (and sometimes even use-to-use by the same patient, particularly if the patient is undergoing an asthmatic attack or respiratory-type ailment which tends to close the airway).

Generally described, known single and multiple dose dry powder DPI devices use: (a) individual pre-measured doses, such as capsules containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices desire to administer a uniform aerosol dispersion amount in a desired physical form (such as a particulate size) of the dry powder into a patient's airway and direct it to a desired deposit site. If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, many dry powder inhalers can retain a significant amount of the drug within the device, which can be especially problematic over time. Typically, this problem requires that the device be disassembled and cleansed to assure that it is in proper working order. In addition, the hygroscopic nature of many of these dry powder drugs may also require that the device be cleansed (and dried) at periodic intervals.

Some inhalation devices have attempted to resolve problems attendant with conventional passive inhalers. For example, U.S. Pat. No. 5,655,523 proposes a dry powder inhalation device which has a deagglormeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029, 663 to Eisele et al. proposes a dry powder inhaler delivery system with a rotatable carrier disk having a blister shell sealed by a shear layer that uses an actuator that tears away the shear layer to release the powder drug contents. The device also includes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of these patents are hereby incorporated by reference as if stated in full herein.

More recently, Hickey et al. in U.S. Provisional Application Ser. No. 60/188,543 and corresponding international PCT patent publication WO 01/68169A1 have proposed a DPI system to actively facilitate the dispersion and release of dry powder drug formulations during inhalation using piezoelectric polymer film elements which may promote or increase the quantity of fine particle fraction particles dispersed or emitted from the device over conventional DPI systems: the contents of these documents are hereby incorporated by reference as if recited in full herein.

Notwithstanding the above, there remains a need to provide easily used, cost effective, and reliable dry powder inhalers.

SUMMARY OF THE INVENTION

Embodiments of the present invention provide improved dry powder inhaler configurations. The dry powder inhalers may be particularly suitable for use with active piezoelectric polymer-driven dispersion or delivery means. Embodiments of the present invention are directed to dry powder inhaler configurations and associated receptacle or blister packages as well as methods for dispensing dry powder substances and/or methods for fabricating blister packages.

In certain embodiments, the dry powder inhaler can be pre-packaged with an integrated predetermined quantity of individually dispensable doses that is disposable after a desired dispensing period, such as 30, 60, or 90 days. This can limit the amount of patient or user interchange with the dry powder inhaler, thereby removing the requirement that the DPI be disassembled to insert additional doses into the unit (and may also promote a more hygienic product). In other embodiments, the DPI can be configured to allow replaceable dry powder packages to be inserted/removed from the device at desired intervals.

In particular embodiments, whether the inhaler is disposable at each refill interval or refillable and reusable, the dry powder package therein can include a thin layer of piezoelectric polymer material that is in communication with each of a plurality of selectively excitable receptacle regions. In operation, the piezoelectric polymer material layer is rapidly flexed back and forth to deform a selected receptacle(s) region, thereby actively facilitating the dispersal of the dry powder drug into the inhalation delivery path.

The active piezoelectric regions can be formed as an elongated resonant chamber to cause the dry powder substance to contact the floor and/or ceiling of the resonant chamber repeatedly. This can increase the transfer of energy from the actively flexing piezoelectric polymer resonant chamber to the dry powder substance, promoting longer contact times therewith as the dry powder substance travels the length of the resonant chamber and exits the patient inhalation port.

The increased active dispersal can promote resonance of the dry powder substance and allow improved blends, such as increased concentrations and/or reduced total quantities of substances relative excipient, over conventional dry powder pharmaceutical substances.

Certain embodiments of the present invention are directed to multi-dose dry powder packages for holding inhalant formulated dry powder substances. The packages comprise: (a) a platform body comprising a plurality of sealed blisters thereon and at least one thin piezoelectric polymer material layer forming at least a portion of each of the sealed blisters, wherein the sealed blisters comprise a respective at least one of a plurality of spatially separated discrete elongate dry powder channels having an associated length, width and height; and (b) a conductive material attached to selected portions of the piezoelectric polymer material to, in operation, define active energy-releasing vibratory channels, and wherein, in operation, the elongate channels can be selectively activated to vibrate upon exposure to an electrical input.

Other embodiments of the invention are directed to dry powder inhalers. The inhalers include: (a) an elongate body having opposing first and second outer primary surfaces with a cavity therebetween and having opposing top and bottom end portions; (b) a multi-dose sealed blister package holding a plurality of discrete meted doses of a dry powder inhalable product located in the cavity of the elongate body; (c) an inhalation port formed in the bottom end portion of the elongate body, the inhalation port configured to be in fluid communication with at least one of the discrete meted doses during use; and (d) a cover member that is pivotably attached to the elongate body so that it remains attached to the body during normal operational periods of use and moves to a first closed position to overlie the inhalation port at the bottom end portion of the body during periods of non-use and moves to a second open position away from the inhalation port during periods of use to allow a user to access the inhalation port.

The cover member may have a length that is greater than a major portion of the length of the elongated body and a width is less than the width of the elongate body. In certain embodiments, the cover member has two opposing first and second end portions, the first end portion being pivotably attached to the upper portion of the elongated body with the cover having a major portion with a substantially planar profile and a downwardly extending arcuately shaped second end portion.

Still other embodiments of the present invention are directed to methods for fabricating a multi-dose disposable dry powder blister package. The method includes: (a) providing a piezoelectric polymer material; (b) concurrently forming a plurality of elongated projections having a width and an associated length into the piezoelectric polymer material; and (c) applying a metallic material to selected regions of at least one primary surface of the piezoelectric polymer material so as to cover at least a portion of each of the plurality of projections.

Another embodiment of the invention is directed to methods of administering an inhalable dry powder product to a subject. The method includes: (a) oscillating a piezoelectric polymer material forming at least a portion of a sealed encased elongated channel and having opposing first and second end portions at a selected frequency or frequency range; (b) disrupting the integrity of the seal associated with the elongated channel at a second end portion; (c) directing a dry powder product to flow through the elongated channel to exit at the second end portion so that a major portion of the dry powder substance repeatedly contacts the oscillating piezoelectric material at a plurality of locations along the elongated channel; (f) imparting energy to the dry powder product based on the oscillating and directing steps to cause the dry powder product to vibrate to generate an inhalable aerosol; and (g) releasing the inhalable aerosol to a subject upon inhalation.

Still other embodiments are directed toward methods of administering an inhalable dry powder product to a subject. The methods include: (a) providing an inhaler with a multiple dose blister package comprising piezoelectric polymer material that is associated with a plurality of discrete sealed blisters holding respective dry powder doses; (b) priming a selected portion of the package to vibrate the dry powder in at least one selected sealed blister proximate in time to an intended inhalation delivery thereof; then (c) introducing an opening in the at least one selected blister; (d) vibrating the at least one selected blister by a applying an input signal to the piezoelectric polymer material proximate the selected blister; and (e) releasing the inhalable dry powder to a subject upon inhalation.

These and other objects and/or aspects of the present invention are explained in detail in the specification set forth below.

BRIEF DESCRIPTION OF THE DRAWINGS

FIG. 9 is a schematic top view of a multi-dose dry powder package according to embodiments of the present invention.

FIG. 10 A is a section view of the package of FIG. 9 taken along line 10A-10A thereof according to embodiments of the present invention.

FOG. 10B is a section view similar to that shown in FIG. 10A but with the well having an alternate configuration according to embodiments of the present invention.

FIG. 11 is a top view of an alternate dry powder multi-dose package according to certain embodiments of the present invention.

Figure 12A:
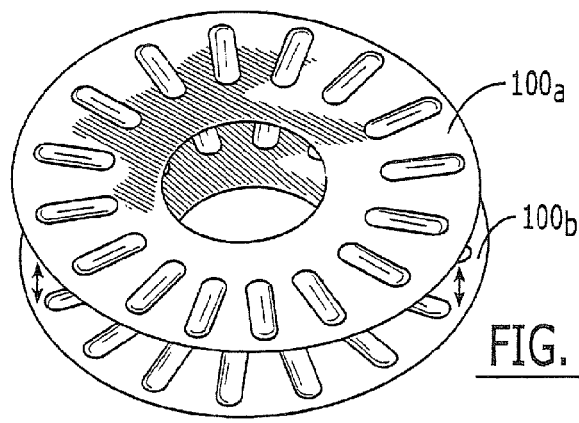

FIG. 12A is a perspective view of a stacked configuration of dry powder multi-dose packages according to embodiments of the present invention.

Figure 12B:
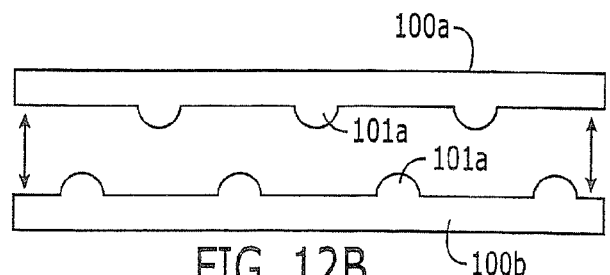

FIG. 12B is a side edge view of the configuration shown in FIG. 12A.

Figure 12C:
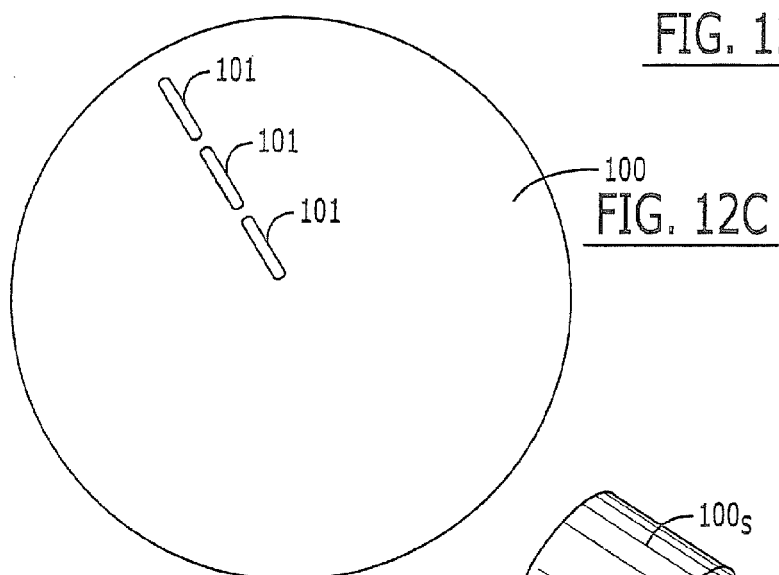

FIG. 12C is a schematic view of a portion of a blister package according to embodiments of the present invention.

Figure 13:
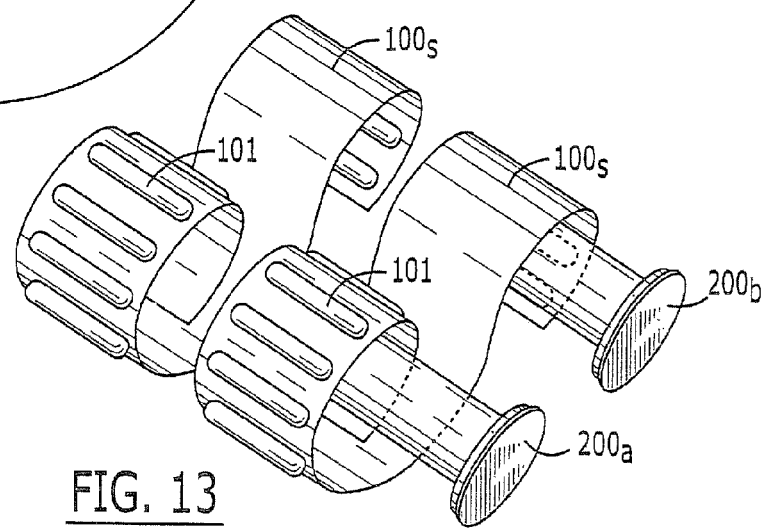

FIG. 13 is a front perspective view of a scrolled configuration of a dry powder multi-dose package according to alternate embodiments of the present invention.

Figure 14A:
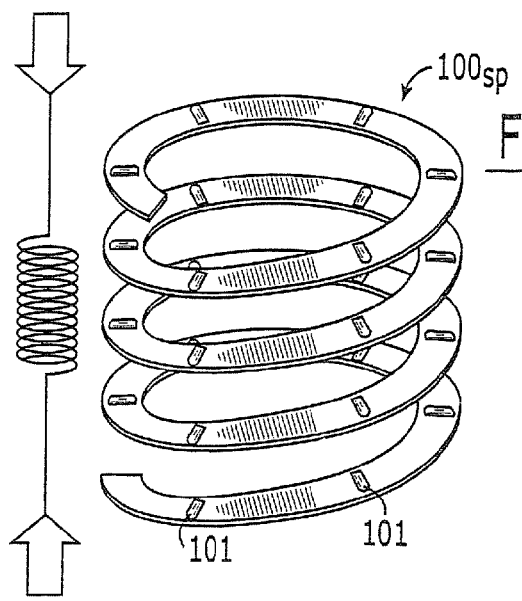

FIG. 14A is a side perspective view of an undulated multi-dose package according to still other embodiments of the present invention.

Figure 14B:
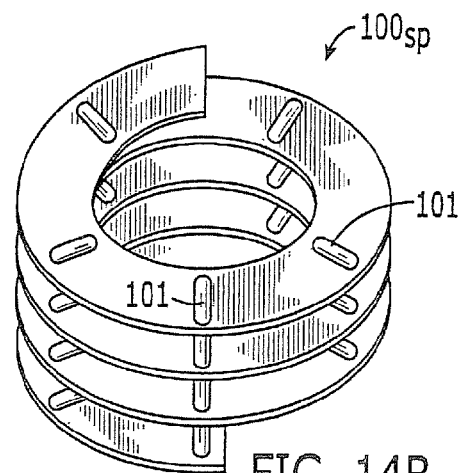

FIG. 14B is a top perspective view of the device shown in FIG. 14A.

Figure 15A:
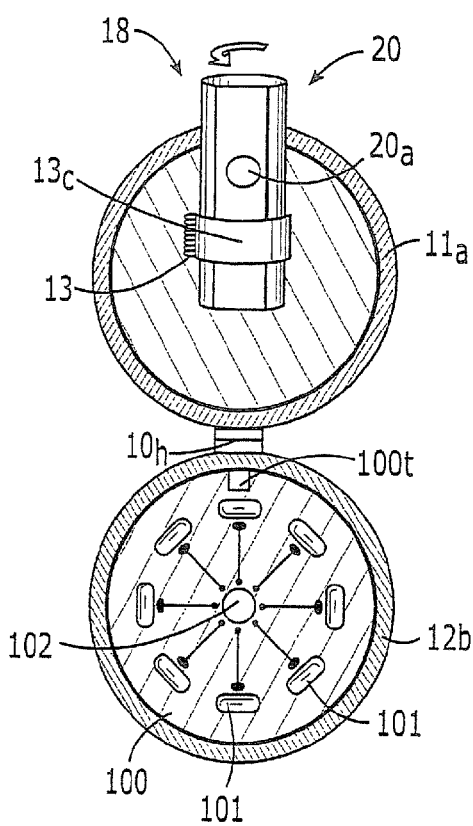

FIG. 15A is a top view of an alternate embodiment of a dry powder inhaler shown in an open position according to embodiments of the present invention.

Figure 15B:
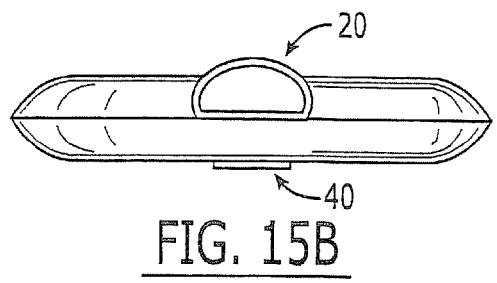

FIG. 15B is a side view of the device shown in FIG. 15A with the device in a closed position.

Figure 15C:
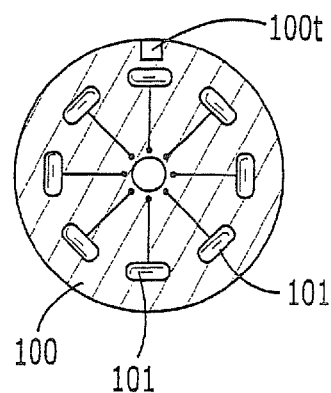

FIG. 15C is a top view of a multi-dose dry powder package suitable for use in the device shown in FIG. 15A according to embodiments of the present invention.

Figure 16A:
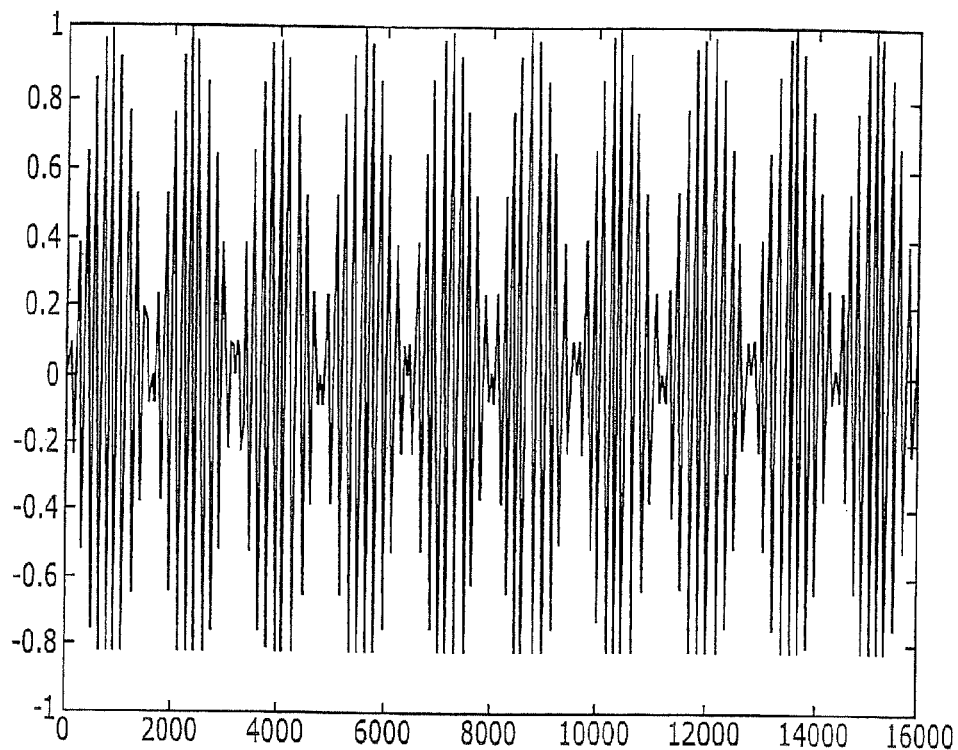

FIG. 16A is a graph of the vibration amplitude/frequency input used to disperse the dry powder to a patient according to embodiments of the present invention.

Figure 16B:
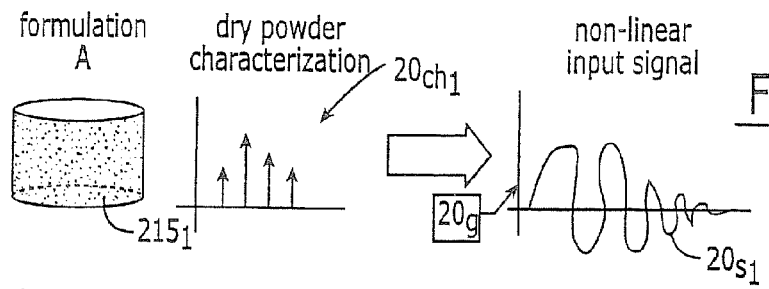
Figure 16C:
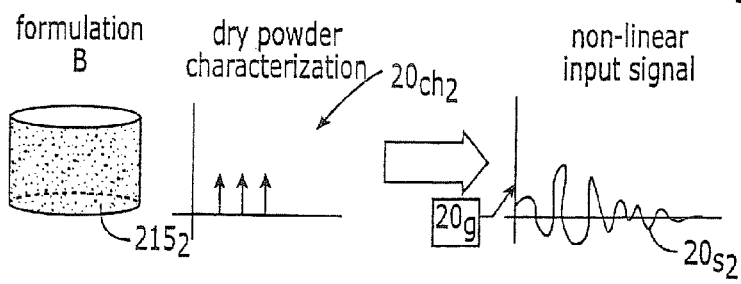
Figure 16D:
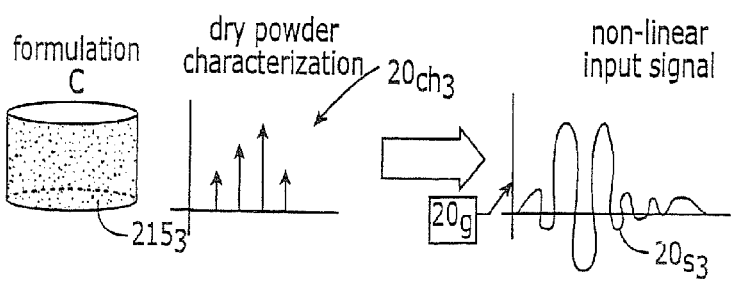

FIGS. 16B-16D are schematic illustrations of three different dry powders and associated customized non-linear powder specific input signals according to embodiments of the present invention.

Figure 17A:
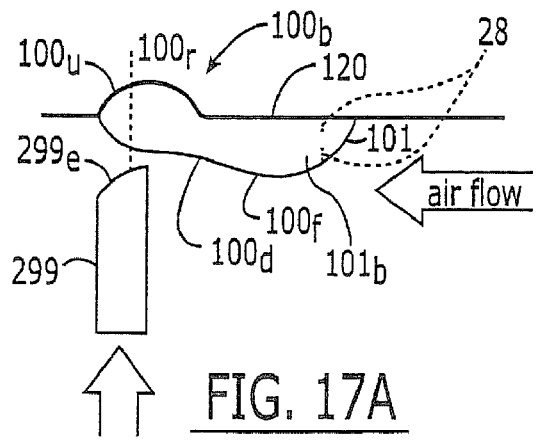

FIG. 17A is a side section view of a blister package with a powder release (which may be a slit or puncture) member according to embodiments of the present invention.

Figure 17B:
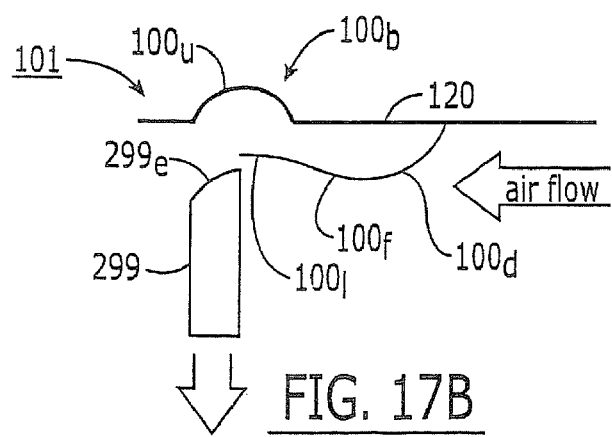

FIG. 17B is a side section view of the blister package shown in FIG. 17A after the bottom forward portion (in the flow direction) of the blister has been opened according to embodiments of the present invention.

Figure 18A:
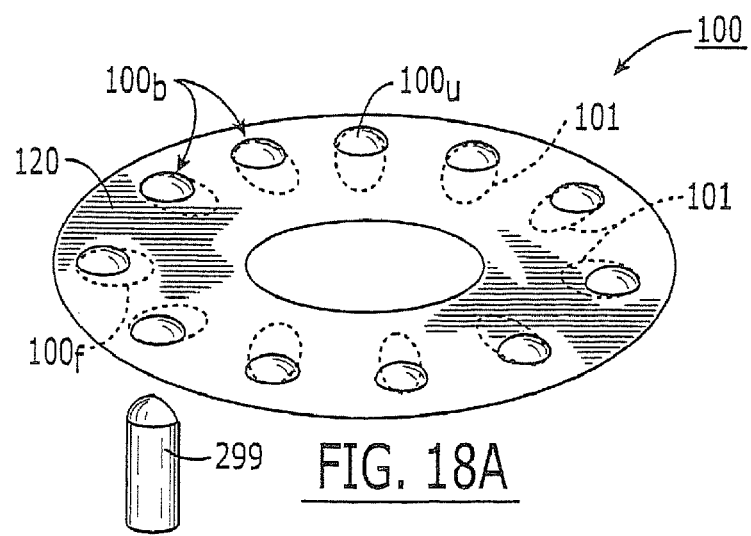

FIG. 18A is a perspective top view of a multi-dose package according to embodiments of the present invention.

Figure 18B:
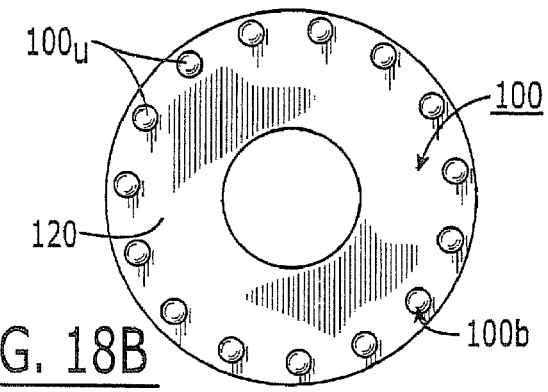

FIG. 18B is a top view of the package shown in FIG. 18A.

Figure 18C:
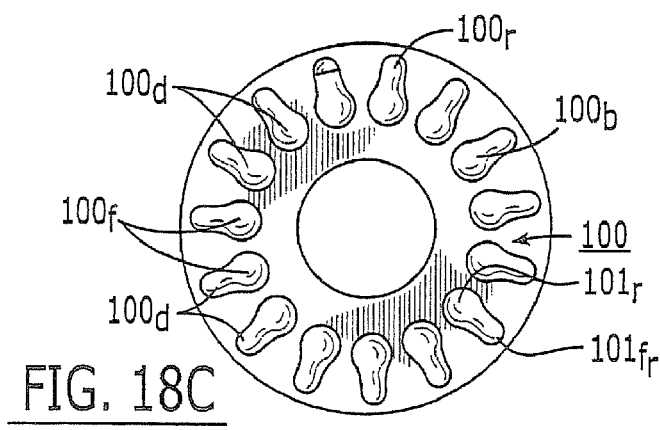

FIG. 18C is a bottom view of the package shown in FIG. 18A according to embodiments of the present invention.

Figure 18D:
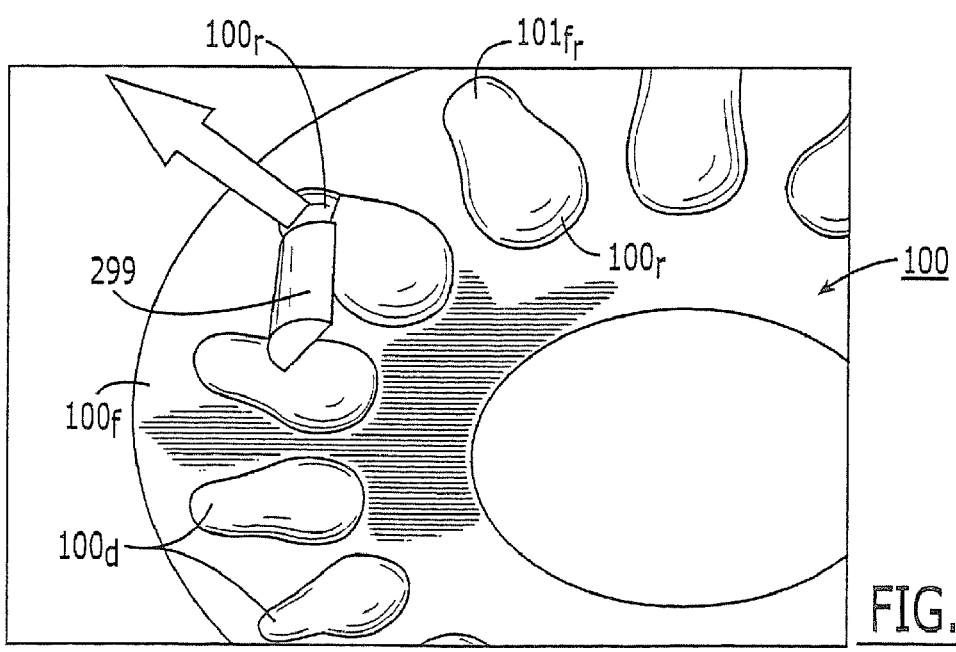

FIG. 18D is a partial bottom perspective view of the package shown in FIG. 18C.

FIG. 18E is a top perspective view of the package shown in FIG. 18A illustrated without the covering of the package according to embodiments of the present invention.

FIG. 19A is a side section view of a blister package with a top positioned powder release member according to other embodiments of the present invention.

FIG. 19B is a side section view of the blister package shown in FIG. 19A after a top portion of a blister has been opened according to embodiments of the present invention.

FIG. 20A is a top perspective view of a multi-dose blister package with a powder release member according to embodiments of the present invention.

Figure 20B:
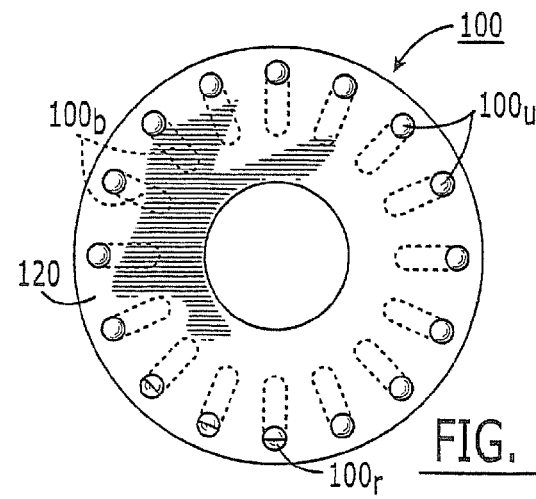

FIG. 20B is a top view of the blister package shown in FIG. 20A with a plurality of blisters shown having openings formed into their tops according to embodiments of the present invention.

Figure 20C:
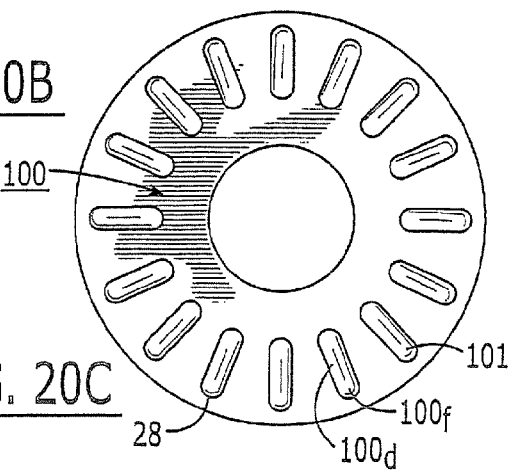

FIG. 20C is a bottom view of the blister package shown in FIG. 20A according to embodiments of the present invention.

FIG. 20 D is an enlarged partial side perspective view of the blister package shown in FIG. 20A with a powder release member positioned to open a top portion of the blister according to embodiments of the present invention.

Figure 20D:
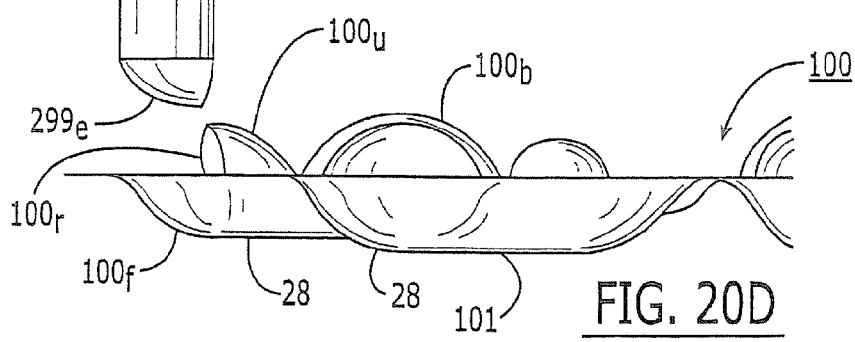
Figure 20E:
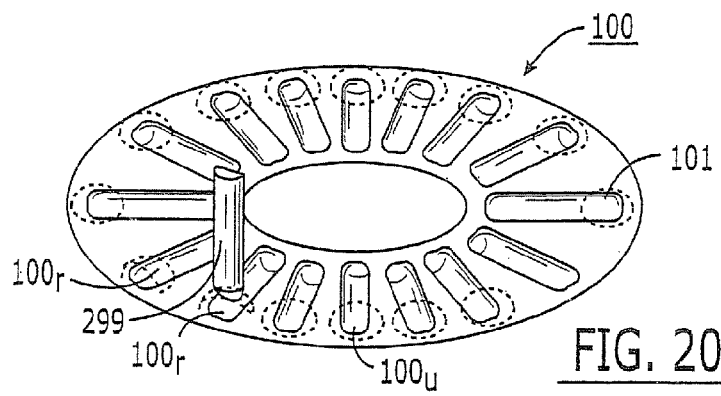

FIG. 20E is a perspective top view of the blister package and puncture member shown in FIG. 20D with the top or overlay of the blister removed except for the opened blisters which illustrate a release (such as a puncture or slit) location according to embodiments of the present invention.

FIGS. 21A-21E illustrate one embodiment of a customized signal generation algorithm for determining a non-linear input signal comprising a plurality of superimposed frequencies according to embodiments of the present invention.

Figure 22:
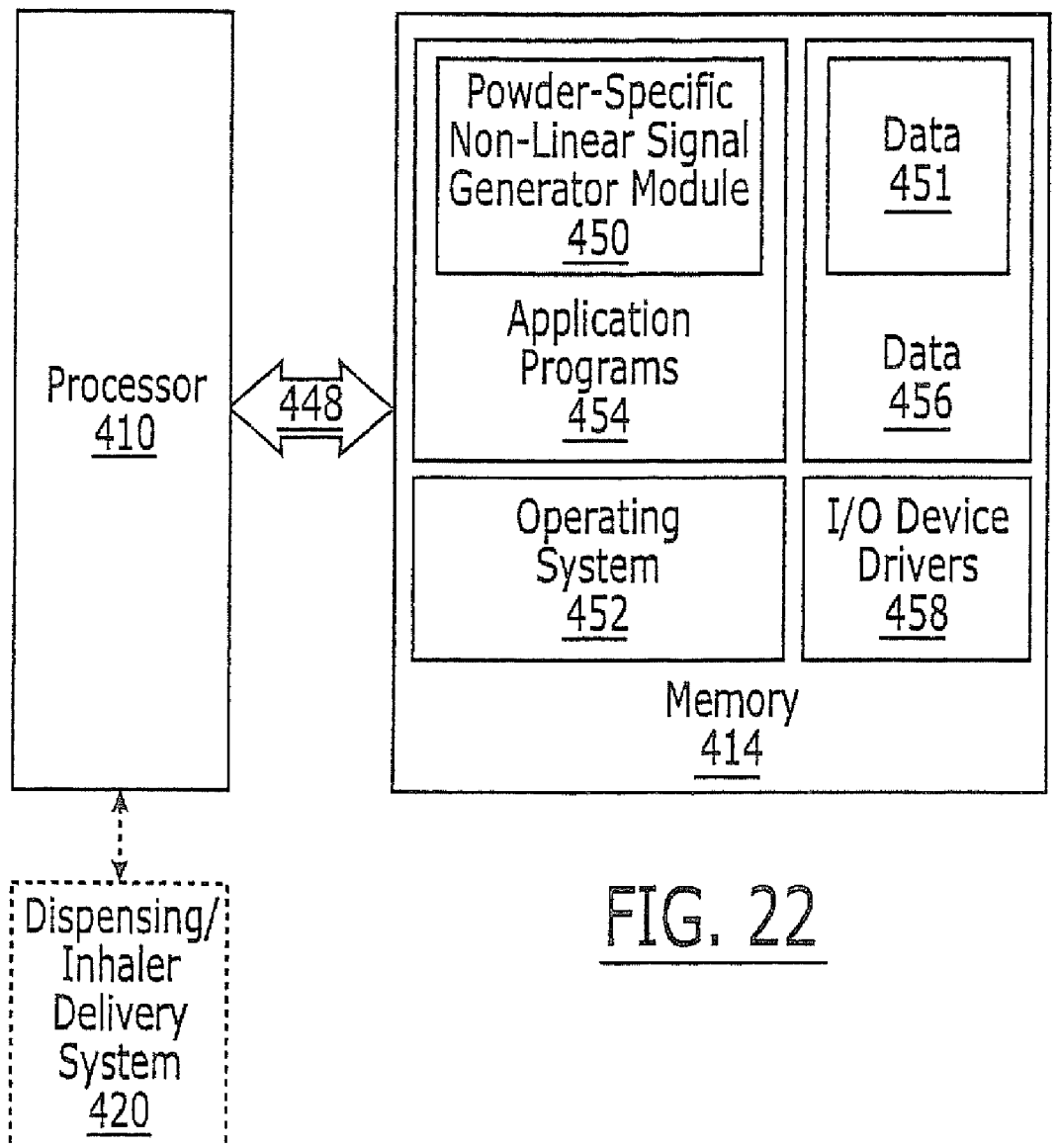

FIG. 22 is a block diagram of a data processing system according to embodiments of the present invention.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise. Where used, the terms "attached", "connected", "contacting", and the like, can mean either directly or indirectly, unless stated otherwise.

In the description of the present invention that follows, certain terms are employed to refer to the positional relationship of certain structures relative to other structures. As used herein, the term "front" or "forward" and derivatives thereof refer to the general or primary direction that the dry powder travels as it is dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the directions opposite, respectively, the forward and downstream directions. The term "blister" means a dry powder receptacle that can hold a (typically meted) quantity of a dry powder product. The blister may be configured with an elongated channel or cavity as will be described further below, or configured in other suitable geometries. In operation, the blisters are opened (slit, punctured or otherwise parted) before the dry powder dose is released by the inhaler in the aerosolized inhalant form.

The devices and methods of the present invention may be particularly suitable to dispense dry powder substances to in vivo subjects, including animal and, typically, human subjects. The dry powder substance may include one or more active pharmaceutical constituents as well as biocompatible additives that form the desired formulation or blend. As used herein, the term "dry powder" is used interchangeably with "dry powder formulation" and means the dry powder can comprise one or a plurality of constituents or ingredients with one or a plurality of (average) particulate size ranges. The term "low-density" dry powder means dry powders having a density of about 0.8 g/cm³ or less. In particular embodiments, the low-density powder may have a density of about 0.5 g/cm³ or less. The dry powder may be a dry powder with cohesive or agglomeration tendencies.

In any event, individual dispensable quantities of dry powder formulations can be a single ingredient or a plurality of ingredients, whether active or inactive. The inactive ingredients can include additives added to enhance flowability or to facilitate aeorolization delivery to the desired systemic target. The dry powder drug formulations can include active particulate sizes that vary. The device may be particularly suitable for dry powder formulations having particulates which are in the range of between about 0.5-50 μm, typically in the range of between about 0.5 μm -20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

Examples of diseases, conditions or disorders that may be treated with the inventive devices and methods include, but are not limited to, asthma, COPD (chronic obstructive pulmonary disease), viral or bacterial infections, influenza, allergies, and other respiratory ailments as well as diabetes and other related insulin resistance disorders. The dry powder inhalant administration may be used to deliver locally acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled *Method for Administering ASPB28-Human Insulin* and U.S. Patent Application Publication No. 20010007853, entitled *Method for Administering Monomeric Insulin Analogs*, the contents of which are hereby incorporated by reference as if recited in full herein.

Typical dose amounts of the unitized dry powder mixture dispersed in the inhaler will vary depending on the patient size, the systemic target, and the particular drug. Conventional exemplary dry powder dose amount for an average adult is about 10-30 mg and for an average adolescent pediatric subject is from about 5-10 mg. Exemplary dry powder drugs include, but are not limited to albuterol, fluticasone, beclamethasone, cromolyn, terbutaline, fenoterol, β-agonists, salmeterol, formoterol, and glucocorticoids. In certain embodiments, the administered bolus or dose can be formulated with an increase in concentration (an increased percentage of active constituents) over conventional blends. Further, the dry powder formulations may be configured as a smaller administerable dose compared to the conventional 10-25 mg doses. For example, each administerable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during dose dispensing, the dry powder in a particular dose receptacle may be formulated as only an active pharmaceutical constituent(s), substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In certain embodiments, the active elements are integral to/included as part of the disposable drug package, unlike many conventional active dispersion systems, cleansing of the active mechanism portion of the inhaler may not be required.

Figure 1:
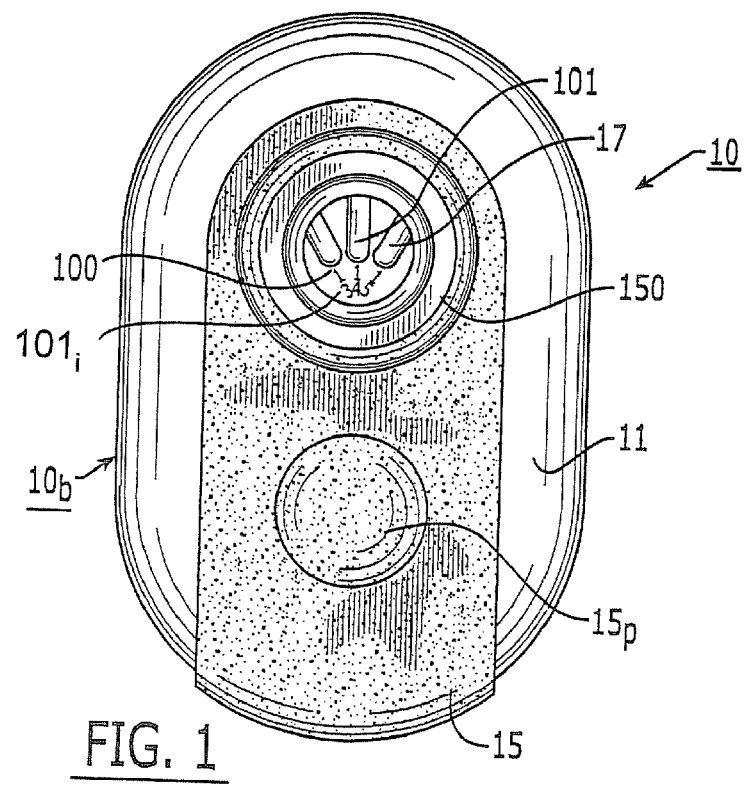
FIG. 1 is a top view of a dry powder inhaler according to embodiments of the present invention.
Figure 6:
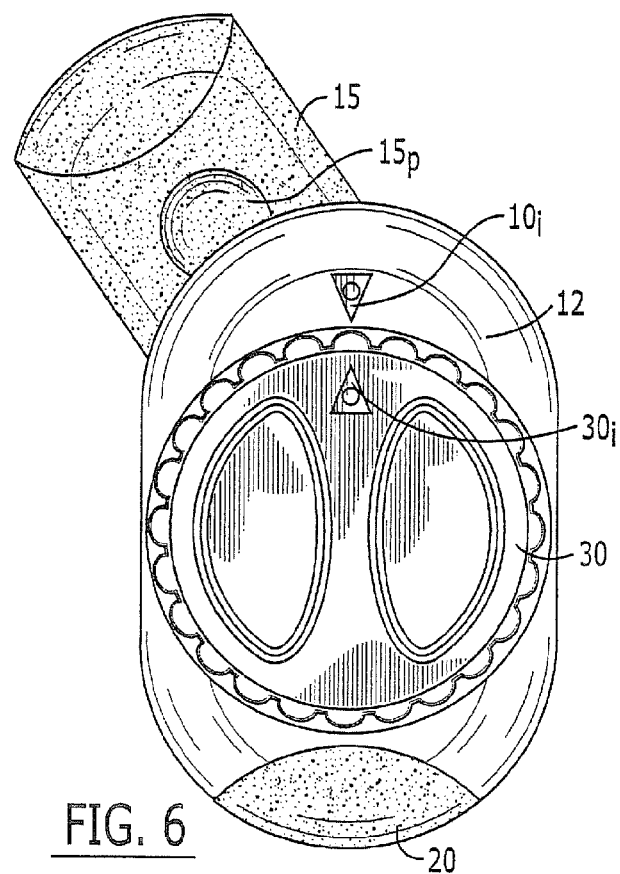
FIG. 6 is a bottom view of the device shown in FIG. 1, with the cover open as shown in FIG. 4.

Referring to FIG. 1, one embodiment of a dry powder inhaler 10 is shown. The inhaler 10 can be configured as an elongated body 10b defining an internal cavity 10c (FIG. 8). the inhaler 10 includes a top primary surface 11 and an opposing bottom primary surface 12 (FIG. 6). A window 17 may be formed into the body of the inhaler 10 to allow a user to have visual contact with an enclosed multi-dose dry powder package 100. The window 17 may include a transparent or translucent member or an aperture. The former may reduce environmental contamination during use.

As illustrated, the inhaler 10 can include a pivotably attached cover member 15 that overlies a major portion of the top surface 11. The cover member 15 can pivot about any desired portion of the device. As shown, the cover member 15 includes an end portion with an aperture 15o that may correspond to the size of a window 17. The cover member 15 attaches to the top portion of the elongated body 10b and pivots about an axis that is normal to the window 17. FIG. 1 illustrates the cover member 15 in a closed position where it blends with profile contour of the perimeter of the elongated body 10b. The cover member 15 may be formed of an elastomeric material that has increased flexibility relative to the elongated body.

Figure 3:
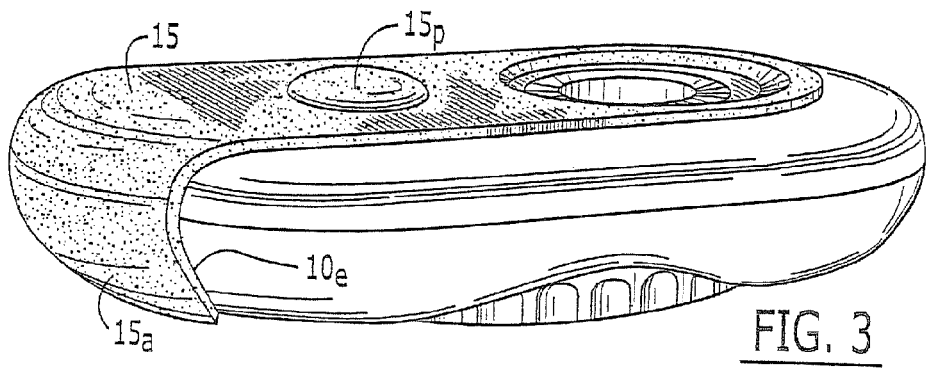
FIG. 3 is a side perspective view of the dry powder inhaler shown in FIG. 1.
Figure 5:
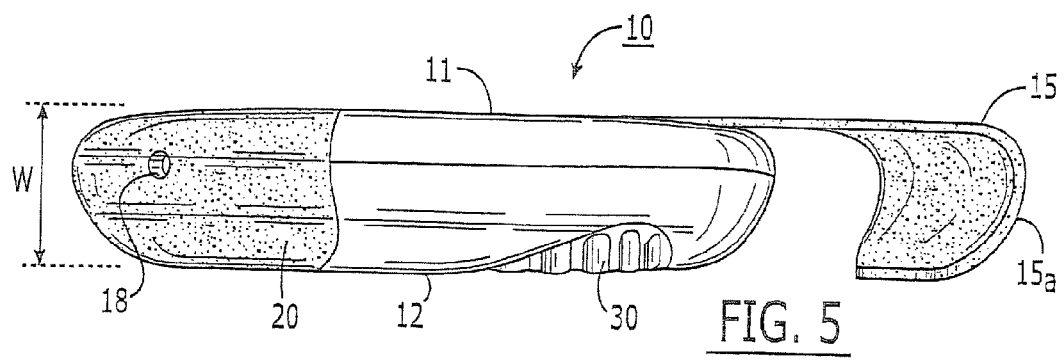
FIG. 5 is another side perspective view of the device shown in FIG. 1 with the cover in an open position.

As shown in FIGS. 3 and 5, the elongated body 10b can have a thin profile when viewed from the side with planar top and bottom surfaces 11, 12. As used herein, the term "thin" means less than about 1.5 inches thick, and more preferably is about 1 inch or less in width (the width "W" being the distance between the top and bottom surfaces 11, 12, as shown in FIG. 5).

The elongated body 10b can be configured to be pocket-sized (fitting into standard pockets on male and/or female clothing). By using substantially planar primary surfaces 11, 12, and/or a thin profile, the device 10 may be less obtrusively worn (less conspicuous) and/or more conformal to the body and less intrusive in clothing pockets. In certain embodiments, the length of the elongated body is between about 2-5 inches, typically under about 4.25 inches, with the width being about 2-4 inches, typically about 2.5 inches.

Figure 7:
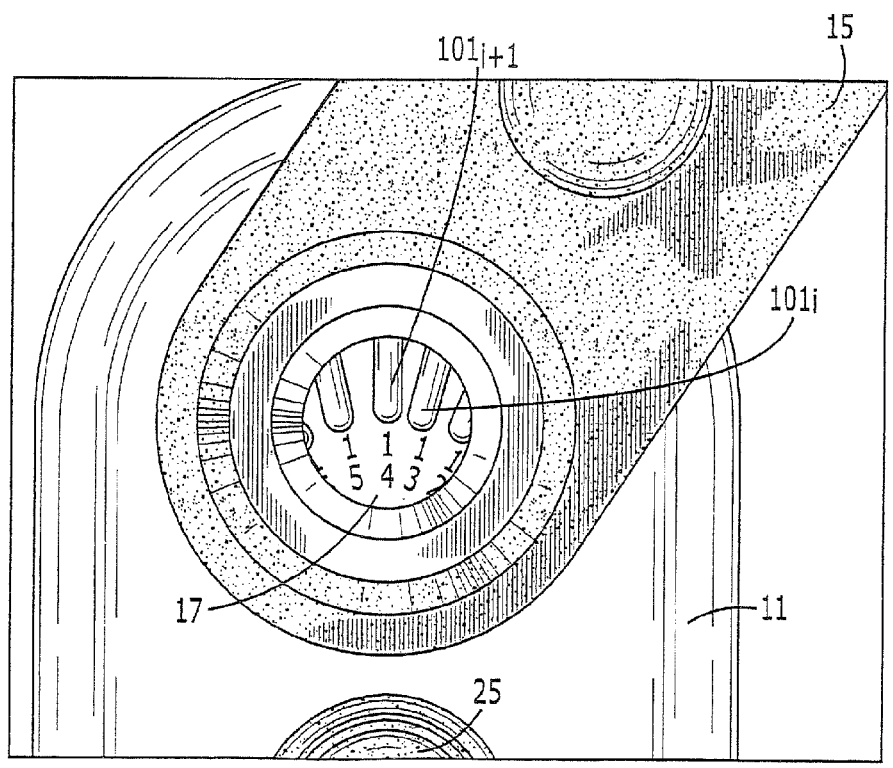
FIG. 7 is a greatly enlarged partial top view of the device shown in FIG. 1 with the cover open as shown in FIG. 4.

FIG. 1 also illustrates that the multi-dose dry powder drug package 100 can include a plurality of circumferentially spaced-apart elongated channels 101, each sealed with a quantity of dry powder product disposed therein. Each of the elongated channels 101 can be numbered with an alphanumeric indicia 101$i$, 101$i$+1 (FIG. 7) to indicate the present dose located in the dispensing channel. FIG. 7 is an enlarged view of the window and underlying portion of the package 100. In other embodiments, visible indicia and/or audible alerts can be used to warn a user that he/she is approaching the last of the filled inhalant doses. For example, color enhanced markings can be used for the last few (such as the last 5 doses) the color enhanced may change from darker (orange to salmon or red) or to completely different colors as the last dose or last few doses approach. Alternatively (or additionally), the multi-dose disposable package 100 may be configured with audible alert features that activate a digital signal processor or micro-controller (not shown) housed in the elongated body 10 to generate a stored audible warning (such as "warning, refill needed, only five doses remain) when a desired number of doses have been administered.

Figure 2:
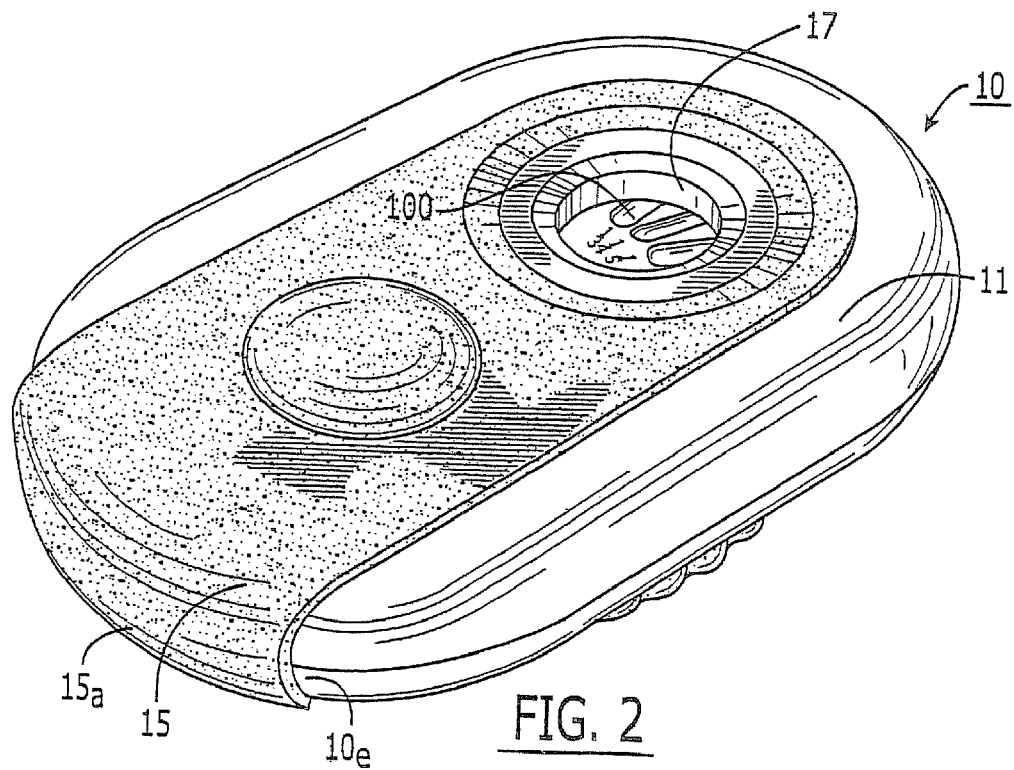
FIG. 2 is top perspective view of the dry powder inhaler shown in FIG. 1.

Turning to FIGS. 2 and 3, as shown, the cover member 15 can be configured so that a major length is relatively thin and planar and overlies a major portion of the top surface 11 of the body when the cover member 15 is in a closed position. The outer end portion 15$a$ of the cover member 15 that covers the mouthpiece 20 can be arcuately configured so as to snugly abut or frictionally align and engage the bottom end portion of the elongated body 10$b$ when closed. That is, the curvature conforms to the curvature of the bottom or side edge of the elongated body 10$c$ adjacent the mouthpiece 20.

Figure 4:
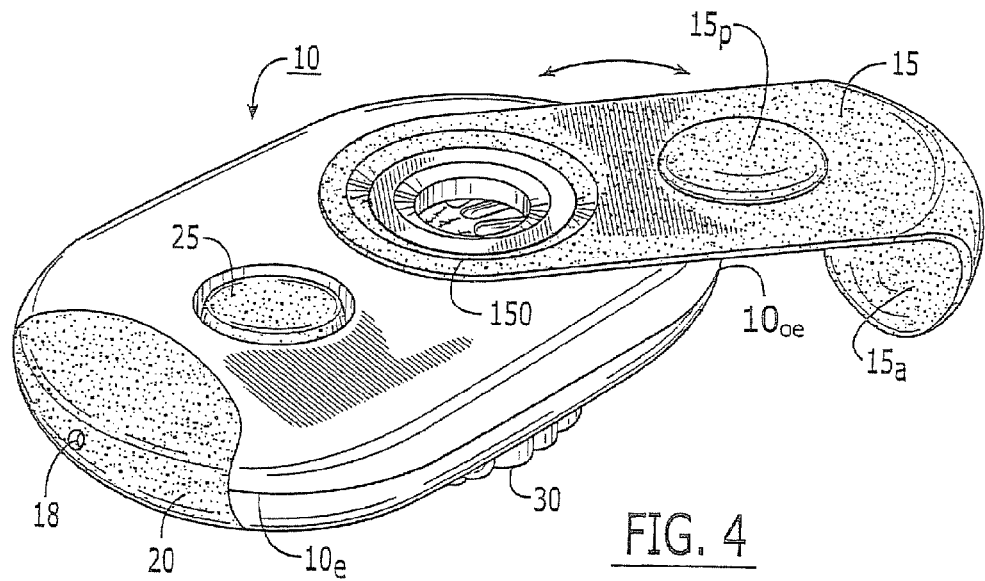
FIG. 4 is a side perspective view similar to that shown in FIG. 3, but illustrating the cover member in an open position.

FIG. 4 illustrates that the lower portion 15$a$ of the cover member 15 moves away from the bottom portion 10$e$ of the elongated body 10$b$ to reveal the inhalation port 18 of the mouthpiece 20. This allows a user access to the mouthpiece 20 and associated inhalation port 18. Because the cover member 15 is retained on the device during normal operation (whether open or closed) and positioned in a non-interfering location, it is less likely to be lost or removed from the device. As shown, the cover member 15 may pivot to reside about the opposing end portion 10$oe$ and overhang the elongated body 10$b$. As the cover member 15 pivots or rotates about the front surface 11, it exposes an activation button 25 that, when depressed, initiates the active dispensing of the dry powder substance(s) located in the inhalation output or dispensing region of the device 10. As with conventional inhalant devices, the active inhalation may involve puncturing or disrupting a thin cover material (that may be an elastomeric or polymer sealant cover or even another layer of piezoelectric polymer) disposed over the powder. In any event, the cover member 15 may be configured with an upwardly extending projection region or mound 15$p$ that is configured to overlie the activation button 25 when closed. The mound 15$p$ may be configured to define a sufficient air pocket to inhibit inadvertent activation of the button 25. The mound 15$p$ may be formed of the same flexible elastomeric material as the remainder of the cover member 15, or may be formed of a stiffer material for additional protection.

In certain embodiments, the elongated body 10$b$ may include a recess positioned about the mouthpiece 20 that can be sized to matably receive the cover member 15 therein so that the cover member 15 pops into or nests in and/or locks into the closed position (not shown). Similarly, the pivotal attachment of the cover member 15 can be configured with a ratcheting wheel or gear that biases the cover member 15 into a desired closed and/or open position.

Although shown as positioned to overlie the top surface 11 of the elongated body 10$b$, the cover member 15 may be configured to extend from the bottom surface 12 upwardly to cover the mouthpiece 20. Similarly, the pivotal attachment can be laterally offset instead of longitudinally offset as shown.

FIG. 6 illustrates that the bottom surface 12 of the elongated body 10$b$ can include an indexing mechanism 30 that allows a user to advance the multi-dose package 100 to the next dry powder dose. The indexing mechanism 30 or a similar knob can include alignment indicia 30$i$ (shown herein as an arrowhead) that can be aligned with alignment indicia 10$i$ on the housing body 10$b$ to allow the elongated body 10$b$ to be disassembled and more easily reassembled with a replacement disposable multidose package 100. The indexing mechanism 30 can reside in other locations and configured in other electrical and/or mechanical configurations.

In certain embodiments, the mouthpiece 20 can be removed by disengaging and/or pulling it from its adjacent portion of the inhaler 10 without requiring further disassembly of other components. This can allow the mouthpiece 20 to be cleaned as desired. Typically, the mouthpiece 20 is snapped into and held in position by a friction fit joint. Of course, other connection components and configurations may also be used as is known to those of skill in the art.

Figure 8:
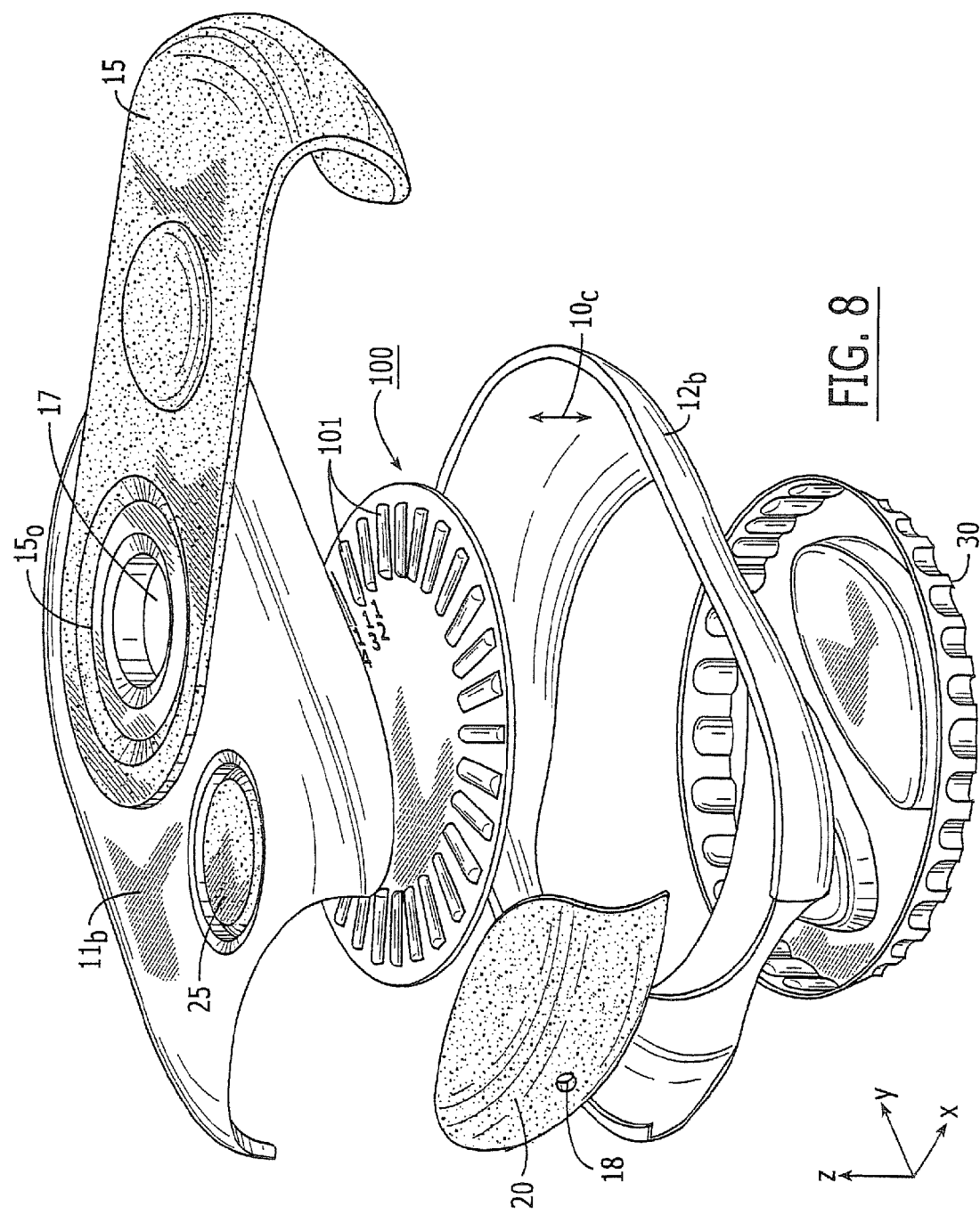
FIG. 8 is an exploded view of the device shown in FIG. 1.

FIG. 8 illustrates that the elongated body 10$b$ can be configured as two primary matable first and second housing members 11$b$, 12$b$ that allow the disposable package 100 to be replaced as needed. In other embodiments, the entire elongated body 10$b$ and contents are disposable after depletion of the dispensable doses (whether a 30, 60, 90 or other day supply). The contents typically include the control system, a microchip such as a digital signal processor (not shown), power source (battery)(not shown), and the package 100.

FIG. 8 illustrates the package 100 in the cavity 10$c$ with the elongated channels 101 formed of the piezoelectric polymer material oriented with the projection curving up (projecting upwardly). In this embodiment, the piezoelectric material can define the ceiling and the opposing sidewalls. However, in certain embodiments, as shown in FIGS. 9, 10A, and 10B the package 100 has a reversed orientation so that the elongated channels 101 have the projection curving down (projecting downwardly). In the latter configuration, the piezoelectric material can define the floor and sidewalls of the channel 101. As will be described further below, the piezoelectric polymer material can be deposited, coated, sprayed, inked, foiled, or otherwise layered with a metallic conductive material at selected regions of the package 100 and along at least a portion of each of the elongated channels 101 to define a vibrating or flexing active region when activated by an excitation voltage.

FIG. 9 illustrates that the elongated channels may include a sealant layer 120 that seals the elongated channels 101. The sealant layer 120 may be a thin polymer film material, a foil layer, and, in certain embodiments, may be another layer of piezoelectric polymer film that is also coated or layered with metal to become activated during dispensing. In any event, the sealant layer 120 may be a ceiling with an end portion 120$s$ that is scored, notched or otherwise formed so that it is preferentially predisposed to part, puncture or split upon exposure to a blunt pressure (such as based on actual contact with a dose release or puncture device or an elevated pressure). In certain embodiments, the end portion 120s closest to the mouth of the user is notched or scored to increase the travel distance of the dry powder along the length of the elongated channel 101, which can increase the interchange between the dry powder and the piezoelectric material; this can increase the amount of energy transferred to the dry powder from the oscillating or vibrating active piezoelectric polymer film so as to cause the dry powder to vibrate at a frequency that is at or near a resonant frequency thereof.

In certain embodiments, the elongated channels 101 can be shaped and/or sized to define a resonant chamber or cavity to generate a desired frequency(ies) of oscillation of the piezoelectric polymer material and/or a particular dry powder formulation. That is, each blend or formulation of dry powder may exhibit different flow characteristics that can be accounted for in the geometry design of the elongated channel 101. The height or depth, length, or width of the channel may be adjusted based on the particular drug or dry powder being administered. Advantageously, the inhaler 10 can be configured to dispense a number of different dry powder packages 100, each having the potential of having different drug receptacle or blister configurations. For example, the package 100 may be fabricated with 2-10 different standard lengths and a particular drug or formulation and dose matched to one of the predetermined standard lengths based on the closest match to generate an optimum vibration frequency. In other embodiments, the length of the channel and/or other parameters can be custom designed and defined for each formulation or drug that is to be administered using the inhaler device 10 and the inhaler device 10 can be configured to operate with and/or accommodate each custom package 100.

FIG. 16A illustrates an example of an amplitude-modified vibratory signal 20s (FIG. 10A) of a dry powder that can include a kHz carrier frequency (such as about 5 kHz-50 kHz) modified by low modulating frequency (typically about 10-200 Hz) that may be generated and used to dispense a dose of dry powder from a blister channel 101 (FIG. 10A) as contemplated by certain embodiments of the present invention. The frequency of the vibration can be modified to match or correspond to the flow characteristics of the dry powder substance held in the package to attempt to reach a resonant frequency(s) to promote uniform drug dispersion into the body. In certain embodiments, the vibration of the active piezoelectric surfaces in the channel 101 may be on the order of about 10-200 Hz. In certain embodiments, the frequency may be between at about 10-60 Hz. The vibration can be influenced by the amount of active surface and the excitation voltage pulses applied thereto as well as the channel geometry. During dispensing, a channel 101 can be activated by providing a voltage across the piezoelectric layer. In certain embodiments, the voltage provided may be at about 100-400 volts peak-to-peak, typically between about 200-400 volts peak-to-peak. In other embodiments, the voltage can be applied at a different level and at other various frequencies, such as at higher frequencies of between about 25 kHz to about 2 MHz. Additional suitable excitation signals will be discussed further below.

In certain embodiments, the signal 20s (shown schematically in FIGS. 10A, 10B with respect to the channel 101) and/or the vibration of the energy provided to the channel 101 may be configured to concurrently or successively rapidly vibrate the dry powder at a plurality of different frequencies (at similar or different amplitudes) in the range of between about 10 Hz-1000 kHz. In certain embodiments, the frequencies are between about 10-200 Hz, such as 10-60 Hz. In other embodiments, they may be in the range of between about 7 kHz-100 kHz, such as 7.5 kHz or more such as frequencies between about 15 kHz to 50 kHz.

In particular embodiments, as schematically shown in FIGS. 16B-16D, a non-linear powder-specific dry powder vibratory energy signal 20s (shown as a different powder specific signal for each of the simulated illustrated formulations shown as "A", "B" and "C") comprising a plurality of selected frequencies can be generated (corresponding to the particular dry powder being currently dispensed) to output the particular signal corresponding to the dry powder then being dispensed. As used herein, the term "non-linear" means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder "flow resonance" is generated allowing active flowable dispensing.

FIGS. 16B-16D illustrate three different dry powders $215_1$, $215_2$, $215_3$, each of which can be analyzed and/or characterized ($20ch_1$, $20ch_2$, $20ch_3$, respectively). Custom or corresponding individual (non-linear) input signals with frequencies selected from the corresponding characterization that are specifically targeted to that dry powder to facilitate fluidic flow during dispensing can be determined for each dry powder $215_1$, $215_2$, $215_3$. The drug-specific signals are shown by the signals $20s_1$-$20s_3$.

The inhalers 10 include signal generating circuitry 10g therein in communication with the channels 101. The signal generating circuitry 20g may be programmed with a plurality of predetermined different signals 20s, or if the inhaler dispenses only a single dry powder, the signal generator 20 may be programmed with a single signal 20s. Appropriate powder-specific signals can be determined experimentally and/or computationally at an OEM or evaluation site and input into the inhalers (via hardware and/or software components including programmable processors).

FIGS. 21A-12E illustrate an example of operations that may be carried out to generate a dry powder-specific signal. A microflow analysis of the dry powder to be dispensed can be performed to assess avalanching flow profiles and/or other suitable mass/time flow profiles. The analysis can be carried out to select predominant oscillatory frequencies for a particular dry powder that, when applied to the powder during flowable dispensing, can promote uniform mass flow to achieve a fluid-like flow, even for low-density dry powders.

Methods and devices for analyzing rapid powder flow measurement are described in Crowder et al., *Signal Processing and Analysis Applied to Powder Behavior in a Rotating Drum*, Part. Part. Syst, Charact. 16, 191-196 (1999); Crowder et al, *An instrument for rapid powder flow measurement and temporal fractal analysis*, Part Syst Charact 16, pp. 32-34, (1999); and Morales-Gamboa, et al., *Two dimensional avalanches as stochastic Markov processes*, Phys Rev. E, 47 R2229-2232 (1993), the contents of which are hereby incorporated by reference as if recited in full herein. See also, Ditto et al., *Experimental control of chaos*, Phys. Rev. Lett., 65: 3211-3214 (1990); B. H. Kaye, *Characterizing the Flow of Metal and Ceramic Powders Using the Concepts of Fractal Geometry and Chaos Theory to Interpret the Avalanching*

*Behaviour of a Powder*, in T. P. Battle, H. Henein (eds.), *Processing and Handling of Powders and Dusts, The Materials and Metals Society*, 1997;B. H. Kaye, J. Gratton-Liimatainen, and N. Faddis. *Studying the Avalanching Behaviour of a Powder in a Rotating Disc.*, Part. Part. Syst. Charact. 12:232-236 (1995), and Ott et al., *Controlling Chaos*, Phys. Rev. Lett. 64: 1196-1199 (1990), the contents of each of these articles are also incorporated by reference as if recited in full herein. Using the principals and relationships described in one or more of these articles with signals derived from analyses of mass flow and/or microflow, one can determine custom powder specific signals that may be able to achieve uniformly flowing dry powders.

As shown in FIG. 21A, the time between avalanches, for a particular dry powder of interest, may be evaluated experimentally using a rotating drum. This time information may be converted to frequency space (frequency domain) as shown in FIG. 21B. FIG. 21C illustrates that a distribution of frequencies $20f$ can be determined (computationally or via computer models). Then, a desired number of selected frequencies can be identified. The frequencies selected may span a desired statistically significant percentage of the distribution or be the frequencies most observed in the analysis spectrum. The term "most observed" means those frequencies occurring the greatest number of times in the distribution. For example, the number of different frequencies selected may be at least the three most observed different frequencies and/or sufficient frequencies to represent at least about 50% of the distribution. In certain embodiments, the number can be at least about 5, and typically about 6, or a number sufficient to represent at least about 75% of the frequency distribution. To select the number, two or three of the most observed frequencies can be used to form the vibration signal. The results can be analyzed experimentally and additional frequencies may be added to the combined non-linear signal to improve fluidic flow performance.

FIG. 21D illustrates that six of the most observed frequencies 20$f_1$-20$f_6$, in the distribution plot 20*f* can be selected. FIG. 21E illustrates that the selected frequencies can be superimposed to generate a single superposition signal (that may also include weighted amplitudes for certain of the selected frequencies or adjustments of relative amplitudes according to the observed frequency distribution). Thus, FIG. 21E illustrates a derived non-linear oscillatory or vibratory energy signal that may be used to dispense a particular dry powder.

Referring again to FIG. 21D, the signal can be created digitally by computer code means employing mathematical or numerical computation techniques and relevant equations. For example, for a signal 20*s* having representative frequencies "$f_{1-n}$," the cumulative signal $x_{signal}$ (20*s*, FIG. 21D) can be generated include a plurality of signal components, $xf_1$-$xf_n$ (shown as 20$f_1$-20$f_n$ in FIG. 21D) at each desired frequency, $f_n$, each component having an amplitude "a" at its frequency as described below. Using the spectrum shown in FIG. 21D noting that the most observed frequency in FIG. 21D is 20$f_3$, the following equations may be used to generate the non-linear signal.

For an index, "n" ranging from 0-15,999, used to generate the digital signal:

$$n=[0:15999] \quad \text{Equation (1)}$$

$$xf_3=\sin(2\pi n/16000) \quad \text{Equation (2)}$$

$$xf_2=af_2 \sin(2\pi n(f_2)/16000(f_3)) \quad \text{Equation (3)}$$

$$xf_4=af_4 \sin(2\pi n(f_4)/16000(f_3)) \quad \text{Equation (4)}$$

This evaluation can be continued for a desired number of frequencies to render a representation of a sufficient number of frequencies/spanning a sufficient portion of the spectrum. The powder-specific, non-linear signal can be generated by summing the selected individual frequency components.

$$x_{signal}=xf_3+xf_4+xf_4 \quad \text{Equation (5)}$$

In certain embodiments, the overall power in the signal, $x_{signal}$, can be increased by adding a phase shift to one or more of the summed components. For example, for component $xf_2$, the associated signal contribution can be adjusted by the following equation:

$$xf_2=af_2 \sin(2\pi n(f_2)/16000(f_3)+m\pi/n_f) \quad \text{Equation (6)}$$

Where "m" is the number at this frequency and $n_f$ is the total number of frequencies contained in the signal.

An example of a commercially available rotating drum is the TSI Amherst AER0-FLOW™ rotating drum(TSI Inc. Particle Instruments/Amherst, Amherst, MA). This device provides powder flow information by detecting the occurrence of and recording the time between avalanches. The AEROFLOW™ rotating drum has been utilized to demonstrate correlation between powder flow and tableting performance for like materials. The instrument uses a photocell detector for its avalanche detection mechanism. A light shines through the plexiglas drum and is obscured from the detector to varying degrees by powder contained in the drum. As the drum rotates, the powder heap rises with the rotation and the photocell detector is uncovered. When an avalanche occurs in the powder heap, the light is again blocked by the cascading powder. The change in light intensity striking the photocell is interpreted by the data collection software as the occurrence of an avalanche. In other embodiments, the occurrence of avalanches can be measured using a sensitive microphone/accelerometer that can be mounted on the rotating drum. Avalanches can be detected acoustically from the sound generated by the avalanching powder. This technique can reduce the amount of powder used, typically to milligram quantities, such as about 10 mg. Statistics of the time between avalanches are determined and an avalanche time phase space plot is generated.

A useful method of presenting data to discover the dynamics of a system is the Poincaré phase space plot. This phase space approach is one in which variables sufficient to describe a system are contained in a single vector. The state of the n variables at an instant in time is a point in phase space. Plotting the time evolution of the system in phase space can map its dynamics. As an example, a simple harmonic oscillator can be pictured in phase space by plotting the position versus the velocity. variables that completely describe the system. The phase space plot of the harmonic oscillator is a circle reflecting the periodic, but 90 degrees out of phase, exchange of maximum position and velocity. A damped harmonic oscillator would appear as a simple attractor with the trajectory encircling and eventually collapsing to the origin as the position and velocity reach zero. The correlation dimension provides a measure of the space filling properties of the phase space representation. A hypersphere of dimension D and radius r is centered on each data point. The number of data points falling within that sphere as a function of the radius may be displayed in a log-log plot. The slope of the resulting line may be termed the correlation dimension.

To determine an appropriate vibration signal, a suitably sized dry powder sample can be disposed in the drum (such as about 60 ml or less of powder as noted above). The drum can be allowed to rotate through a single revolution before data collection begins so that initial conditions over several powders are similar. The drum can be rotated at 0.5 revolutions per minute for 6 minutes. The photocell voltage signal can be sampled at 25 Hz using a PC based data acquisition board (DI-170, Dataq Instruments, Akron Ohio). Time between avalanches and the voltage change upon avalanching can be acquired from the voltage signal. A video camera can be situated perpendicular to the drum can record the powder as it rotates in the drum. A grid can be placed behind the drum, without obscuring the photocell, to facilitate determination of the angle of the powder relative to the horizontal. Upon viewing the video, the base and height of the powder heap can be recorded and the angle can be determined using the trigonometric relation, $\theta=\arctan(\text{height}/\text{base})$. Determinations of the instantaneous powder angle can be performed at 200 millisecond intervals. This rate corresponds to every sixth frame of the video, determined previously by recording the counting of a stopwatch.

Angle data time series can comprise at least about 500 data points or 100 seconds. Computation of a Fourier power spectrum can be performed using the Welch method with a 128 point Kaiser window and zero padding to 1024 data points for the FFT calculation. Other suitable methods can be employed as is known to those of skill in the art.

The avalanche statistics can be presented in terms of the mean and standard deviation of time between avalanches. A phase space plot can be generated by plotting the $n^{th}$ time to avalanche against the $(n-1)^{th}$ time to avalanche. For the angle of repose, phase space plots consist of the instantaneous deviation from the mean angle versus the first time derivative of the angle. The rate of change of the angle at each data point can be approximated from the preceding and subsequent data points using Newton's method.

The uniformity of flow can be discerned by examining the frequency and the amplitude of the oscillations. Certain dry powder signals may exhibit a higher degree of variability in frequency and in amplitude relative to others. By use of the Fourier transform (FT) power spectrum, energy distributions can be obtained. Energy spectrums that are dispersed over a range of frequencies can indicate more irregular flow. The mean time to avalanche can be subtracted from the instantaneous time to avalanche to deconvolute relevant frequency data in angle phase space plots. Identifying the predominant frequencies and selectively combining and/or using those identified frequencies as the basis of the transmitted vibration energy excitation signal may induce resonance in the dry powder during dispensing.

Alternatively, the non-linear signal can be determined experimentally as described in co-assigned, co-pending U.S. Patent Application Ser. No. 60/440,513, the contents of which was incorporated by reference hereinabove. Generally described, a flow channel housing having an angularly adjustable elongate flow channel therein can be used to determine appropriate powder-specific signals. A dry powder of interest (which may be a low density dry powder) can be introduced into the elongate flow channel. The flow channel can be vibrated to thereby vibrate the dry powder to cause the dry powder to fluidly flow out of the channel via an exit port. The flow channel can include a flexible piezoelectric polymer over which the dry powder flows; the piezoelectric polymer can be electrically stimulated to flex upwardly to cause it to vibrate the powder as the powder travels along and through the flow channel. As described above, the vibration can carried out using a non-linear excitation signal having a carrier frequency and a modulation frequency. In certain embodiments, the carrier frequency can be between about 2.5 kHz-50 kHz and modulation frequency may be between about 10-500 Hz. In any event, flow characteristics can be experimentally evaluated, typically over several different input signals at different frequencies, and at least one frequency (and/or angular orientation of the flow path) selected for its ability to generate reproducible fluidic flow of dry powder based on the flow characteristics exhibited during the vibrating step. The orientation of the flow channel can be adjusted so that the flow channel is angularly offset (with the dispensing port located lower than the input port) in the axial direction with respect to the horizontal and vertical axis. In certain embodiments, the flow channel is adjusted to be at different selected angles during the evaluation to consider the impact that the angle may have on the dispensing flow.

In any event, in certain embodiments, the output signals 20s used to activate the piezoelectric channels 101 may be include a plurality, typically at least three, superpositioned modulating frequencies and a selected carrier frequency. The modulating frequencies can be in the range noted herein (typically between about 10-500 Hz), and, in certain embodiments may include at least three, and typically about four superpositioned modulating frequencies in the range of between about 10-100 Hz, and more typically, four superpositioned modulating frequencies in the range of between about 10-15 Hz.

FIG. 10A illustrates one embodiment of an elongate channel 101. The channel 101 has a length that is greater than its width. In certain embodiments, the length may be at least twice the distance of the width. As shown, the elongate channel 101 includes a ceiling 120 and a floor 100f. The floor 100f includes a metallic material layer 100m thereon. The ceiling 120 can be configured to be preferentially pre-disposed to separate at a desired location 120s as noted above. Referring to FIG. 9, the metallic region 100m on the channel 101 is in communication with a metal trace 100t that extends a distance away from the channel 101 and, in operation, can engage a power source and relay the input signal from the signal generator circuitry 20g.

Increased numbers of doses may be held on a single disposable package 100, whether symmetrically aligned or offset one to another on a single primary surface, or formed on opposing primary surfaces (the package can be flipped to access the underside portion of doses). In certain embodiments, about 50-100 discrete doses or more can be held on the package 100 (not shown).

FIG. 10B illustrates that the channel 101 can be configured so that the floor 100f slopes or descends a distance over the length of the channel 101 so that the downstream end of the channel 101 during dispensing and/or the region more proximate the preferentially predisposed separation portion has a greater depth. This can allow gravity to help move the powder along the length of the channel 101, allowing the dry powder to contact a greater active amount of active or vibrating piezoelectric polymer surface area. As such, the elongated channels 101 contemplated by embodiments of the present invention may amplify the vibration frequency of the dry powder before it is released to the user. In yet other embodiments, the cavity of the channel can narrow and/or become more shallow (the channel transitioning from a depth "D2" to a depth "D1") as it approaches the end portion that is proximate the mouth of the user during dispensing (FIG. 17A).

FIG. 11 illustrates another embodiment of the present invention. In this embodiment, a sensor that can detect one or more patient-air flow related parameters in situ during each dispensing, can be incorporated directly into the disposable multi-dose packaging 100. As shown, each blister 101' or channel 101 (FIG. 1) can have a proximately positioned airflow parameter sensor circuit 150. The circuit 150 includes conductive traces 150t and a sensor 150s that can detect air pressure differential or airflow rate. If the sensor 150s detects air pressure differential, this can be compared to predetermined airflow rate information, such as a priori knowledge of the inhaler's airflow resistance to determine inspiratory capacity of the user. This data can be analyzed in the controller and the energy applied to the blister or channel adjusted. In certain embodiments, the sensor 150s can be a hot-wire anemometer that is mounted to the package 100 so that it is in fluid communication with the user during operation and powered via the metallic traces 150t when connected to the power source. In other embodiments the piezoelectric polymer layer 28 can define a pressure sensor that detects pressure differential based on its flexure and relay the signal to the controller (not shown).

FIGS. 12A and 12B illustrates that a plurality of individual multi-dose packages 100a, 100b can be stacked in a tier configuration. In the embodiment shown, two packages are stacked, but three, four, or more may also be stacked according to embodiments of the present invention. The dry powder filled blisters 101 can be oriented so as to be in the same or opposing directions package-to-package. In the embodiment shown in FIG. 12B, the blisters are channels 101 and are disposed in package 100a with the arcuately curved portion 101a oriented downward while the lower package 100b is held with the arcuately curved portion 101a oriented upward. The orientations of the channels can be reversed or placed to both face up or down or even alternated on each particular package 100a, 100b (not shown). The packages 100a, 100b can include the same or different channel layout and/or can be angularly offset about an axis extending normal to the packages 100a, 100b and through the centers thereof, when positioned in the inhaler 10. For example, the top package 100a may be rotated so that the underlying channels are misaligned by 5, 30, 45, 60, 90, or 120 degrees or more. Further, a plurality of discrete channels 101 can be provided so that they are aligned end to end in a radially spaced apart configuration (FIG. 12C).

In certain embodiments, each package, or blisters 101 on a particular package 100, may be filled with the same dry powder products, while in other embodiments, each package may be filled with different formulations of dry product (and may have different blister geometry). In certain particular embodiments, the inhaler 10 can be configured so that the packages 100 can provide a combination therapy of two or more different drugs that can be administered concurrently or separately to a subject.

As shown by the two-way arrows in FIGS. 12A and 12B, the stacked tier package configuration can be spring loaded in the inhaler 10 so that the two packages 100a, 100b can be compressed toward each other at activation and the powder in a channel on the top package 100a can be concurrently released with the powder in a corresponding channel on the bottom package 100b. The packages 100a, 100b can then be released to move away from each other decompressing the spring during non-active dispensing.

FIG. 13 illustrates a thin strip package 100s with a plurality of elongated channels 101 positioned along its length. The strip package 100s may be scrolled along two tension rods 200a, 200b as shown to position the dispensing portion in the desired location in the inhaler (advancing the used empty blisters similar to a camera film cartridge). In certain embodiments, as shown in FIG. 13, two side-by-side scrolled strips 100s, 100s can be employed. This side-by-side arrangement may be particularly suitable for combination therapies or deliveries as described above. In other embodiments, the scrolled strips 100s may be placed in a stacked tier one above the other (not shown).

FIGS. 14A and 14B illustrate yet another embodiment of a blister package arrangement. As shown, the package 100sp is vertically undulated and/or spiraled. The adjacent tiers can be coaxially aligned or adjacent tiers or levels can be disposed off center or horizontally offset from the others. The tiers can be arranged in a serpentine arrangement from top to bottom (or side-to-side if oriented laterally instead of longitudinally as shown) to provide spaced apart dry powder blisters channels 101 in spaced apart tiers. The spiral or serpentine arrangement can be provided by arranging a plurality of discrete packages in the desired configuration, by configuring one or more strips or sheets in a spiral configuration and/or by folding a single sheet or strip over on itself to take on a serpentine shape.

FIGS. 15A-15C illustrate an additional embodiment of an inhaler 10'. As shown, the body of the inhaler 10' has a hinge 10h along one edge portion connecting two housing members 11a, 12b and allowing access to the interior cavity 10c. The top housing member 11a holds the mouthpiece 20 and associated inhalation port 18. The bottom member 12b can hold the electronics module 40 (FIG. 15B). As described above, the inhaler 10' houses the dry powder blister package 100. The top housing member 11a may include a spring-loaded connector 13 that facilitates a snug connection between the housing members 11a, 12b, mouthpiece and package 100 when closed and can also provide a conductive connection 13c to the top surface of the blister traces 100t. As shown, the mouthpiece 20 can include an aperture 20a that will overlie a blister region 101 on the package 100 when the inhaler 10' is closed. As shown in FIG. 15A, the package 100 can include a central air aperture 102 that allows air to travel in the cavity 10c. The mouthpiece 20 can be configured to rotate (noted by the arrow in FIG. 15A) about the top housing member 11b so that it can serially overlie each filled blister for inhalation.

The package 100 can include a tab 100t (shown as a notch or cut-out region along the perimeter of the package) that fits into the housing in a desired location to facilitate proper loading in the housing 12b. FIG. 15B illustrates the closed shape and FIG. 15C illustrates the blister package 100.

FIGS. 17A and 17B illustrate another embodiment of a blister 100b with an elongate channel 101. In this embodiment, the blister 100b includes both upwardly and downwardly extending portions. The downwardly extending portion 100d is an elongate lower channel 101 and the upwardly extending portion 100u is a protrusion that can be substantially arcuate and positioned to reside over a forward portion of the blister 100b with the upstream ceiling 120 portion being substantially planar over the remainder of the underlying channel 101.

As shown by the arrow in FIG. 17A, a dose release member 299 can be disposed in the inhaler 10 so as to approach the blister channel 101 from under the floor 100f of the package 100. As shown by the arrow in FIG. 17B, the release member 299 can then return to its static position to be subsequently actuated again for a next release. The release member 299 can be configured with an end portion 299e that has a shape or profile that is substantially the same as the top blister portion 100u of the ceiling 120 overlying the channel 101 in the target release zone. The release member 299 can be configured to puncture, slit, slice, burst, burn, puncture, pierce, melt, or otherwise separate or form the release port or opening in the target region of the floor 101f.

In the embodiment shown in FIGS. 17A and 17B, both the upper portion of the release member 299e and a portion of the ceiling 120 have a substantially upwardly arching or arcuate profile. In certain embodiments, the upper portion 299e may be semi-spherical. In operation, as shown in FIG. 17B, the upper portion of the release member 299 advances to contact and invert the lower portion of the blister (i.e., the loose region of the floor 1001) into the upper blister or ceiling thereby creating a relatively large exit port for the dry powder to exit the channel. The configuration of the release member 299 may reduce the likelihood that the loose end of the floor material will fold back or otherwise impede the release of powder during administration.

In the embodiment shown in FIGS. 17A, 17B and 18A-18E, the target opening region 100r may be a forward portion of the floor 100f. The floor 100f can be formed from and/or include the active piezoelectric polymer material (referred to generally as feature 28) so that, in operation, the floor 100f can flex in response to the applied signal 20s to impart the active delivery vibration energy to the dry powder. In other embodiments, the release region 100r can be formed in a floor that is non-active, such as a foil and/or polymer layer and the ceiling 120 can be formed from the piezoelectric polymer material 28 with the ceiling 120 configured to flex to impart the desired dispersion energy to the dry powder. Combinations of the above may also be employed.

FIG. 18A illustrates the top of one package 100 configuration that can operate as described for FIGS. 17A and 17B. FIGS. 18B and 18C illustrate opposing top and bottom primary surfaces of the package 100 shown in FIG. 18A. FIGS. 18C and 18D illustrate that the elongate channel 101 may have a curvilinear outer profile when viewed from the top that narrows in width from the rear of the channel 101r to the forward portion of the channel 101fr. In addition, the rear portion 101r can have a greater depth (as well as a larger cross-width) than the forward portion 101fr. As shown, the elongate channel 101 may be configured as a substantially pear-shaped dry powder basin or reservoir. FIG. 18E is shown without the top blister ceiling 120 and illustrates the release member 299 in position as it forms the opening or release region 100r in the floor 100f of the channel 101. In operation, the ceiling 120 upstream of the blister 100b can remain intact. The inhaler 10 may be configured with an exit port that is in fluid communication with the package bottom of the blister 100d (not shown).

FIGS. 19A and 19B illustrate another embodiment of a blister 100b with an elongate channel 101 with the release member 299 configured to open the blister 100b from the ceiling 120 of the package. The arrows in FIGS. 19A and 19B illustrate the direction of movement relative to the package 100 orientation. As discussed with respect to FIGS. 17A, 17B, and 18A-18E, in this embodiment, the blister 100b can include both upwardly and downwardly extending protrusion portions 100u, 100d. As before, the downwardly extending portion 100d can be formed as a depression that defines the elongate (lower) channel 101 and the upwardly extending portion 100u can be formed as a protrusion that may be substantially arcuate and positioned to reside over a forward portion of the blister 100b with the upstream ceiling 120 portion being substantially planar over the remainder of the underlying channel 101. The release member forward portion 299e can be configured with a profile that corresponds to the shape of the floor 100f or channel 101 at the lower portion of the blister 100d. The forward contact portion 299e may have a profile that is semi-spherical and/or when viewed from the side, it may have a profile that is substantially arcuate or semi-circular. In operation, as shown in FIG. 19B. the release member 299 can invert the profile of the loose end 100r created by the opening in the ceiling portion 100u so that it substantially blends with and/or conforms to the shape of lower blister 100d as shown in FIG. 19B. That is, the loose edge portion can extend away from the direction of flow but is configured so that it resides proximate the bottom of the channel 101 so that it does not impede the dry powder flow out of the channel 101. The floor 100f of the channel may include the piezoelectric polymer material 28.

FIG. 20A illustrates the release member 299 positioned over the package 100 with a series of blisters 100b having openings or release zones 100r that have been (serially) opened by the release member 299. FIG. 20B illustrates the top or ceiling side of the package 100 shown in FIG. 20A. FIG. 20C illustrates another elongate channel 101 configuration for the floor 100f that forms the bottom portion of the blister 100d. As shown in FIG. 19B and FIG. 20D, in this embodiment, the elongate channel 101 can have a substantially constant depth along its length. FIG. 20E shows the channel 101 from the top with the ceiling 120 substantially transparent except about the opening 100r for clarity.

It is noted that, in operation, depending on how the package 100 and release member 299 are oriented in the inhaler 10, the release member 299 may approach the package 100 from the top or side so that it engages the package ceiling 120 proximate the blister 100b (such as shown for the embodiment shown in FIGS. 19A and 19B) or bottom or opposing side (such as for the embodiment shown in FIGS. 17A and 17B) so that it engages the package floor 100f proximate the blister 100b.

In operation, a priming signal can be applied to the blister 100b prior to forming the opening in the blister 100b to vibrate the dry powder held therein to the lowest portion of the elongate flow channel, which can be described as a blister reservoir or basin 101b. The release member 299 can be directed to open the blister 100b during or after application of the priming signal. The priming signal may be the same signal as the active delivery signal 20s or may be a different signal.

The release member 299 may be configured as any suitable device for inserting or forming the opening in the blister 100b. The release member 299 can be configured to pierce, puncture, slice, melt, or otherwise form the opening in the blister. The release member 299 can include a blade, a laser, pressurized fluid, acoustic energy, or other release or separation means. The release member 299 may be spring loaded to automatically actuate upon a user's depression of a dispensing mechanism.

To facilitate dry powder administration through the inhaler port, the active dispensing signal 20s can be applied to the vibrating layer substantially instantaneous (i.e., during) with the introduction of the opening 100r in the blister 100b. In other embodiments, the signal 20s can be applied before the opening 100r is formed (typically within about 50 ms) or shortly after the opening is introduced into the blister (typically within about 50 ms).

In certain embodiments, each blister 100b can have its own operative electrical parameter and associated electrical connections that engage with a central control unit in the inhaler 10 and can be used to verify proper operative alignment. That is, an electronics module with signal generating circuitry 20g can communicate separately with the electrical traces 100t proximate each blister region 101 to sense a desired electrical parameter such as capacitance of the piezoelectric polymer blister. In other embodiments, the sensed parameter can be an open connection in the electrical path indicating improper alignment.

In particular embodiments, such as for rotating mouthpiece configurations, the device can be configured with a plurality of predefined stops (recesses, projections, etc . . . ) that allow the mouthpiece 20 to click into position in a manner that yields an audible or tactile verification by the user at each dispensing blister (not shown).

In certain embodiments, the piezoelectric polymer material, shown generally as element 28 in FIG. 9 et seq., and which is included in the blister packages 100 of embodiments of the invention, is formed from a piezoelectrically active material such as PVDF (known as KYNAR piezo film or polyvinylidene fluoride) and its copolymers or polyvinylidene difluoride and its copolymers (such as PVDF with its copolymer trifluoroethylene (PVDF-TrFe)).

In particular embodiments, the piezoelectric polymer material layer 28 is a thin film PVDF. As used herein, the term "thin film" means that the piezoelectric polymer layer 28 is configured as a structurally flexible or pliable layer that can be sized to be about 10-200 µm thick. In certain embodiments, the piezoelectric polymer layer can be sized to be less than about 100 µm thick, and more typically, about 20-60 µm thick.

As noted above, selected regions of the piezoelectric polymer material can be coated or layered with a conductive material to form a desired conductive pattern. The conductive regions (at least portions of the blister regions) of the package 100 define the active regions and can be individually or selectively activated during operation. Laminates of PVDF and another material capable of being formed into and hold a desired blister shape and/or powder channel may be particularly suitable for forming the active blister configurations. Suitable laminates include thin film layers of PVDF united to thin layers of one or more of aluminum, PVC and nylon films. The PVDF may form the bottom, top, or an intermediate layer of the laminated material structure. For intermediate layer configurations, vias and/or edge connections can be used to apply the electric signal to the blister piezoelectric material.

The metal trace patterns can be provided by applying a conductive pattern onto one or more of the outer faces of the piezoelectric substrate layer. For depositing or forming the metal, any metal depositing or layering technique can be employed such as electron beam evaporation, thermal evaporation, painting, spraying, dipping, or sputtering a conductive material or metallic paint and the like or material over the selected surfaces of the piezoelectric substrate (preferably a PVDF layer as noted above). Of course, alternative metallic circuits, foils, surfaces, or techniques can also be employed, such as attaching a conductive mylar layer or flex circuit over the desired portion of the outer surface of the piezoelectric substrate layer 28. It is preferred that, if flex circuits are used, they are configured or attached to the substrate layer 28 so as to be substantially transparent to the structure of the sensor array to minimize any potential dampening interference with the substrate layer 28. It is also noted that while particular conductive patterns are illustrated in the figures, the present invention is not limited thereto, as alternative conductive patterns may also be used.

Typically, upper and lower surface metal trace patterns are formed on opposing sides of the piezoelectric polymer material but do not connect or contact each other. For example, conductive paint or ink (such as silver or gold) can be applied onto the major surfaces of the package about the elongated channels and associated metal traces such that it does not extend over the perimeter edge portions 28e of the piezoelectric substrate layer 28, thereby keeping the metal trace patterns on the top and bottom surfaces separated with the piezoelectric substrate layer 28 therebetween. This configuration forms the electrical excitation path when connected to a control system to provide the input/excitation signal for creating the electrical field that activates the deformation of the piezoelectric substrate layer 28 during operation. As such, the electrical path for each elongated channel 101 extends via the respective upper and lower transmission lines to the electrical terminations operably connected to the controller. The excitation circuit (signal generating circuitry 20g) configuration can be such that the upper trace operates with a positive polarity while the lower trace has a negative polarity or ground, or vice versa (thereby providing the electric field/voltage differential to excite the piezoelectric substrate in the region of the selected channel 101). Of course, the polarities can also be rapidly reversed during application of the excitation signal (such as + to −, or + to −) depending on the type of excitation signal used, thereby flexing the piezoelectric material in the region of the receptacle portion. For a more complete discussion of the active excitation path or configuration, see U.S. Provisional Application Ser. No. 60/188,543 to Hickey et al., incorporated by reference hereinabove.

In certain embodiments, methods for fabricating a multi-dose disposable dry powder blister package include: (a) providing a thin layer of piezoelectric polymer material; (b) concurrently forming a plurality of elongated projections having a width and an associated length into the piezoelectric polymer material; and (c) applying a metallic material to selected regions of at least one primary surface of the piezoelectric polymer material so as to cover at least a portion of each of the plurality of projections. For mass production applications, the forming step can be carried out by fabricating a shaping, forming, or molding tool that defines the channel geometry for each package. The tool can have raised projections and/or depressed formations. The forming step can be carried out by stamping the piezoelectric polymer material or the laminated material, which comprises the piezoelectric polymer material, onto the tool or the tool onto a layer or layers of piezoelectric polymer materials. Thus, in certain embodiments, the forming step is carried out by pressing the (which may be a laminated configuration) piezoelectric polymer material over a shaping tool having a plurality of raised projections thereon. The conductive material can be applied before or after the channel geometry forming step. The conductive material may be applied by applying a metallic coating onto a molding tool having a plurality of raised projections with a metallic coating and contacting the piezoelectric material with the molding/shaping tool to thereby transfer the metallic coating onto the desired surface (surfaces) of the elongated projections of the piezoelectric polymer material. Other methods of depositing the conductive pattern may be employed as described above.

In operation, generally described, the dry powder inhalers of the present invention have integrated, active energy piezoelectric polymer substrate multi-dose drug packages that generate patient-assisted dispersal systems. The inhalers can be used for nasal and/or oral (mouth) respiratory delivery. The inhalable dry powder dose is packaged in a multi-dose dry powder drug package that includes a piezoelectric polymer substrate (such as PVDF) that flexes to deform rapidly and provide mechanical oscillation in an individually selectable signal path on the package. The signal path directs the signal to the region of the drug receptacle or well to cause the well to oscillate in cooperation with a user's inspiratory effort, and, thus, actively direct the dry powder out of the well and up into the exit flow path. The airflow rate and/or volume of a patient can be measured in situ dynamically during administration and the DPI can include a control system that provides adjustable energy output to the active piezoelectric polymer substrate dispersal element responsive to a user's inspiratory capabilities. In addition, the DPI control system may be a multi-purpose system that can administer a plurality of different types of dry powder substances, or formulations, such as different drugs. As such, the control system may be configured to adjust the energy delivered to the piezoelectric polymer substrate based on the type of substance and/or the flowability of the dry powder substance or drug being administered. The energy may be adjusted in situ based on considering both the user's inspiratory effort and the type of substance being administered. As a result, the powder can be actively dispersed into the exit flow path of the inhaler during the user's inspiratory activity without using pressurized propellants such as CFC's.

In addition, the piezoelectric polymer material may be configured as two piezoelectric polymer film layers separated by an intermediately positioned pliable core, all of which are concurrently deformable to flex by the application of voltage thereacross.

FIG. 22 is a block diagram of exemplary embodiments of data processing systems that illustrates systems, methods, and computer program products in accordance with embodiments of the present invention. The processor 410 communicates with the memory 414 via an address/data bus 448. The processor 410 can be any commercially available or custom microprocessor. The memory 314 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 22, the memory 414 may include several categories of software and data used in the data processing system 405: the operating system 452; the application programs 454; the input/output (I/O) device drivers 458; the powder specific (vibratory) signal generator module 450; and the data 456. The data 456 may include a plurality of dry powder data 451 corresponding to particular or target signal parameters for each dry powder and/or patient inspiratory data, which may be obtained from an operator or stored by the inhaler and/or timing data that defines the meted dose amounts, flow rates, and open time for the dispensing port (allowing automatic control of the dispensing operation, dependent on the dry powder being dispensed). As will be appreciated by those of skill in the art, the operating system 452 of the inhaler and/or programmable inputs thereto may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the dispensing system 420. The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the powder-specific signal generator module 450 being an application program in FIG. 22, as will be appreciated by those of skill in the art, other configurations may also be utilized while still benefiting from the teachings of the present invention. For example, the module 450 may also be incorporated into the operating system 452, the I/O device drivers 458 or other such logical division of the data processing system 405. Thus, the present invention should not be construed as limited to the configuration of FIG. 22, which is intended to encompass any configuration capable of carrying out the operations described herein.

The I/O data port can be used to transfer information between the data processing system 405 and the inhaler dispensing system 420 or another computer system or a network (e.g., the Internet) or to other devices controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 22 but is intended to encompass any configuration capable of carrying out the operations described herein.

The flowcharts and block diagrams of certain of the figures herein illustrate the architecture, functionality, and operation of possible implementations of dry powder-specific dispensing and/or vibratory energy excitation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the powder specific vibration energy signals are non-linear and the inhaler can include computer program code that automatically selectively adjusts the output of the vibration energy signal based on the identified dry powder being dispensed. The vibration energy output signals for the dry powders being dispensed can be based on data obtained from a fractal mass flow analysis or other suitable analysis of the dry powder being administered to the user. The inhaler may be particularly suited to dispense low-density dry powder.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A dry powder inhaler, comprising:
an elongate body defining a substantially enclosed cavity and having opposing upper and lower primary surfaces, the elongate body having a width dimension and a length dimension, the length dimension being greater than the width dimension, the length dimension extending between opposing first and second ends of the elongate body, the width dimension extending normal to the length dimension between opposing sides of the elongate body;
a multi-dose disk located in the cavity of the elongate body, the disk holding a plurality of doses of an inhalable dry powder;
a mouthpiece with an inhalation port residing at the first end of the elongate body between the upper and lower primary surfaces so as to be externally accessible by a user while the elongate body remains closed, the inhalation port configured to be in fluid communication with at least one of the doses of dry powder during use; and
a cover member having an upper surface that is attached to the elongate body to pivot about an axis of rotation that is substantially normal to the upper primary surface, wherein the axis of rotation is longitudinally offset from a center of the length dimension of the elongate body to reside closer to the second end of the elongate body while being substantially centered in the width dimension, wherein the cover member rotates between a closed position to overlie the mouthpiece during periods of non-use and an open position away from the mouthpiece during periods of use to allow a user to access the inhalation port while the elongate body remains closed, and wherein the cover member rotates from the closed position to the open position about the axis of rotation so that the upper surface of the cover member remains substantially parallel to the upper primary surface of the elongate body.

2. A dry powder inhaler according to claim 1, wherein the cover member has a substantially planar upper surface that overlies the upper primary surface of the elongate body, and wherein the cover member upper surface has an aperture that extends downwardly therethrough that surrounds the axis of rotation.

3. A dry powder inhaler according to claim 2, wherein the aperture is a circular aperture.

4. A dry powder inhaler according to claim 1, wherein the cover member has a planar first end portion that overlies the upper primary surface and an arcuate second end portion, wherein the arcuate portion of the second end portion extends downward over the mouthpiece on the first end of the elongate body when in the closed position.

5. A dry powder inhaler according to claim 1, wherein the elongate body includes matable upper and lower shells that remain closed during use, and wherein the cover member is configured to be able to pivot toward a side of the inhaler elongate body to overhang the elongate body such that an inner portion of a length of the cover member upper surface remains over the upper primary surface of the elongate body while an outer portion of the length of the cover member extends beyond a perimeter of the elongate body.

6. A dry powder inhaler according to claim 1, wherein the upper and lower primary surfaces of the elongate body are substantially planar, wherein the cover member upper surface has a planar portion residing above the upper primary surface of the elongate body, the cover member planar portion having an aperture extending downwardly therethrough, the aperture surrounding the axis of rotation.

7. A dry powder inhaler according to claim 1, wherein the axis of rotation is normal to and extends through a window that provides a user visual access to the multi-dose disk, and wherein the window is defined by aligned apertures in the cover member upper surface and the upper primary surface of the elongate body.

8. A dry powder inhaler according to claim 1, further comprising an indexing mechanism in the elongate body that rotates the multi-dose disk, and wherein the disk has stops or detents that provide tactile and/or audible feedback to a user to verify that the disk is in a desired dispensing position.

9. A dry powder inhaler according to claim 1, wherein the elongate body has a substantially planar portion that comprises a window that allows visual access to a portion of the multi-dose disk, wherein the cover member upper surface comprises an aperture that is aligned with the window, and wherein the axis of rotation extends through and is normal to the window.

10. A dry powder inhaler according to claim 9, wherein the multi-dose disk comprises externally visible indicia of a dose number that is visible through the window during use.

11. A dry powder inhaler according to claim 1, wherein the inhaler includes at least one of a visible or audible alert that warns a user when the multi-dose disk approaches empty.

12. A dry powder inhaler according to claim 1, wherein the elongate body has a thin profile when viewed from the side with the upper and lower primary surfaces being substantially planar, and wherein the cover member upper surface has a substantially planar portion with an outwardly projecting mound portion, the outwardly projecting mound portion configured to overlie an activation button on the elongate body upper primary surface when the cover member is closed to inhibit inadvertent activation.

13. A dry powder inhaler according to claim 1, wherein, with the cover member in the closed position, the inhaler has a thin profile with substantially flat upper and lower primary surfaces that is sized to fit into a pocket of a garment worn by a user.

14. A dry powder inhaler according to claim 1, wherein the inhalable dry powder is a low density dry powder, and wherein the inhalable dry powder held in the multi-dose disk comprises active ingredient particulate sizes of between about 0.5-8.0 µm.

15. A dry powder inhaler according to claim 1, wherein, in the open position, the cover member pivots about the axis of rotation and has a length sufficient to overhang the side of the inhaler such that an inner portion of a length of the cover member upper surface remains over the upper primary surface of the elongate body while an outer portion of the length of the cover member extends beyond a perimeter of the elongate body.

16. A dry powder inhaler, comprising:
an inhaler housing body defining a substantially enclosed cavity;
a multi-dose disk located in the cavity of the housing body, the disk holding a plurality of circumferentially spaced apart doses of an inhalable dry powder;
a mouthpiece with an inhalation port supported by the housing body so as to be externally accessible by a user while the housing body remains closed, the inhalation port configured to be in fluid communication with at least one of the doses of dry powder during use; and
a cover member that is attached to an upper primary surface of the housing body to be able to pivot about an axis of rotation that is substantially normal to the upper primary surface of the housing body, wherein the cover member has a planar upper surface that overlies the upper primary surface of the housin body closed, wherein the axis of rotation is substantially centered in a width dimension of the housing body, and wherein the cover member rotates between a closed position to overlie the mouthpiece during periods of non-use and an open position away from the mouthpiece during periods of use to allow a user to access the inhalation port while the housing body remains closed, wherein the housing body is an elongate body and the mouthpiece resides on one end of the elongate body between upper and lower primary surfaces, and wherein the axis of rotation is longitudinally offset to reside closer to an end of the housing body without the mouthpiece, and wherein the cover member rotates from the closed position to the open position about the axis of rotation so that the upper surface of the cover member remains substantially parallel to the upper primary surface of the elongate body.

17. A dry powder inhaler according to claim 16, wherein the housing body has substantially planar upper and lower primary surfaces, wherein the cover member upper surface is planar and that overlies the upper primary surface of the housing body when closed, and wherein the cover member planar upper surface has an aperture extending downwardly therethrough that surrounds the axis of rotation.

18. A dry powder inhaler according to claim 16, wherein, in the open position, the cover member pivots to a side of the inhaler about the axis of rotation and has a length sufficient to overhang the side of the inhaler such that an inner portion of a length of the cover member upper surface remains over the upper primary surface of the elongate body while an outer portion of the length of the cover member extends beyond a perimeter of the elongate body.

19. A dry powder inhaler according to claim 16, further comprising an indexing mechanism in the elongate body that rotates the multi-dose disk, and wherein the disk has stops or detents that provide tactile and/or audible feedback to a user to verify that the disk is in a desired dispensing position.

* * * * *

UNITED STATES PATENT AND TRADEMARK OFFICE
CERTIFICATE OF CORRECTION

Page 1 of 1

PATENT NO.        : 8,210,172 B2
APPLICATION NO.   : 12/401138
DATED             : July 3, 2012
INVENTOR(S)       : Crowder et al.

It is certified that error appears in the above-identified patent and that said Letters Patent is hereby corrected as shown below:

In the Patent:
Column 5, Line 4: Please correct "FOG.10B is a section"
to read -- FIG.10B is a section --

Column 14, Line 18: Please correct "AER0-FLOW™ rotating"
to read -- AERO-FLOW™ rotating --

In the Claims:
Column 27, Claim 16, Line 1: Please correct "housin body closed"
to read -- housing body when closed --

Signed and Sealed this
Eighteenth Day of December, 2012

David J. Kappos
*Director of the United States Patent and Trademark Office*